United States Patent
Stacey et al.

(10) Patent No.: US 10,564,145 B2
(45) Date of Patent: Feb. 18, 2020

(54) SYSTEM AND METHOD FOR IMAGING A ROTATING OBJECT

(71) Applicant: Haemonetics Corporation, Braintree, MA (US)

(72) Inventors: Gary Stacey, Marshfield, MA (US); James Sullivan, Ashland, MA (US)

(73) Assignee: Haemonetics Corporation, Braintree, MA (US)

( * ) Notice: Subject to any disclaimer, the term of this patent is extended or adjusted under 35 U.S.C. 154(b) by 0 days.

(21) Appl. No.: 15/761,630

(22) PCT Filed: Sep. 28, 2016

(86) PCT No.: PCT/US2016/054112
§ 371 (c)(1),
(2) Date: Mar. 20, 2018

(87) PCT Pub. No.: WO2017/058872
PCT Pub. Date: Apr. 6, 2017

(65) Prior Publication Data
US 2018/0348197 A1 Dec. 6, 2018

Related U.S. Application Data

(60) Provisional application No. 62/302,996, filed on Mar. 3, 2016, provisional application No. 62/234,188, filed on Sep. 29, 2015.

(51) Int. Cl.
*G01N 33/49* (2006.01)
*A61B 5/00* (2006.01)
(Continued)

(52) U.S. Cl.
CPC ........... *G01N 33/491* (2013.01); *A61B 5/004* (2013.01); *A61B 5/0066* (2013.01);
(Continued)

(58) Field of Classification Search
CPC ...... G01N 33/491; G01N 21/47; A61B 5/004; A61B 5/0066; A61B 5/0261; G02B 26/0833
(Continued)

(56) References Cited

U.S. PATENT DOCUMENTS 4,229,095 A * 10/1980 Mir .................. G03G 17/04
355/35
5,260,598 A 11/1993 Brass et al.
(Continued)

FOREIGN PATENT DOCUMENTS

| WO | 2005/074662 A2 | 8/2005 |
| WO | 2015/109323 A2 | 7/2015 |

OTHER PUBLICATIONS

MIB, Refrigerated Centrifuge: Sigma 8KS (max 12×1L). Montreal Biotech. Retrieved online at: http://www.montreal-biotech.com/index.php/products-71/centrifuges/floor-centrifuges.html. 1 page, (2014).
(Continued)

*Primary Examiner* — Roy M Punnoose
(74) *Attorney, Agent, or Firm* — McCarter & English, LLP; Jonathan C. Lovely

(57) ABSTRACT

An imaging system for a rotatable object includes an imaging unit configured to take a series of images of a portion of the rotatable object and a light source. The light source is directed at the rotatable object and is configured to generate pulses of light that illuminate the rotatable object during rotation of the rotatable object and allow the imaging unit to take the series of images of the rotatable object. The system also includes a synchronizer that monitors the rotational position of the rotatable object as it rotates, and a controller in communication with the imaging unit, the light source, and the synchronizer. The controller controls the operation of the imaging unit and/or the light source based upon the rotational position of the rotatable object such that each of
(Continued)

the series of images is taken at the same rotational position of the rotatable object.

55 Claims, 18 Drawing Sheets

(51) Int. Cl.
| | | |
|---|---|---|
| *A61B 5/026* | (2006.01) | |
| *G01N 21/47* | (2006.01) | |
| *G02B 26/08* | (2006.01) | |
| *G01N 21/17* | (2006.01) | |

(52) U.S. Cl.
CPC ............ *A61B 5/0261* (2013.01); *G01N 21/47* (2013.01); *G02B 26/0833* (2013.01); *B81B 2201/0257* (2013.01); *G01N 2021/1765* (2013.01)

(58) Field of Classification Search
USPC ........................................ 600/310, 326, 368
See application file for complete search history.

(56) References Cited

U.S. PATENT DOCUMENTS

| | | | |
|---|---|---|---|
| 5,314,825 A * | 5/1994 | Weyrauch ........ | G01N 35/00663 356/246 |
| 5,814,279 A | 9/1998 | Biesel et al. | |
| 5,850,289 A | 12/1998 | Fowler et al. | |
| 5,889,584 A | 3/1999 | Wardlaw | |
| 7,355,685 B2 * | 4/2008 | Scibona .............. | A61M 1/3693 356/39 |
| 7,605,388 B2 * | 10/2009 | Carter .................... | B04B 13/00 250/222.2 |
| 7,906,771 B2 | 3/2011 | Carter et al. | |
| 8,070,663 B2 | 12/2011 | Sweat | |
| 8,241,196 B2 * | 8/2012 | Scibona .............. | A61M 1/3693 494/10 |
| 8,501,015 B2 * | 8/2013 | Fletcher ................ | B04B 5/0442 210/512.1 |
| 8,535,210 B2 * | 9/2013 | Kolenbrander ..... | A61M 1/3693 210/782 |
| 8,718,948 B2 * | 5/2014 | Heinz ................ | G01N 21/6486 702/19 |
| 8,876,683 B2 | 11/2014 | Chammas | |
| 10,001,497 B2 * | 6/2018 | Ochranek .............. | G01N 35/04 |
| 10,031,085 B2 * | 7/2018 | Jakubowicz ........... | G01N 21/78 |
| 2004/0087426 A1 | 5/2004 | Lattanzi | |
| 2007/0077173 A1 * | 4/2007 | Melet .................... | G01N 21/253 422/64 |
| 2009/0043530 A1 | 2/2009 | Sittler et al. | |
| 2009/0274348 A1 | 11/2009 | Jakubowicz et al. | |
| 2010/0025336 A1 * | 2/2010 | Carter .................... | B04B 13/00 210/740 |
| 2010/0225920 A1 | 9/2010 | Xia et al. | |
| 2011/0056290 A1 | 3/2011 | Bryant et al. | |
| 2011/0184547 A1 | 7/2011 | Loutti | |
| 2011/0278472 A1 | 11/2011 | Atzler | |
| 2013/0265417 A1 | 10/2013 | Rust et al. | |

OTHER PUBLICATIONS

Sales, Efficient and uniform illumination with microlens-based band-limited diffusers. Photonics Spectra, retrieved online at: https://www.photonics.com/Articles/Related_Efficient_and_uniform_illumination_with/ar41972. 11 pages, Apr. 2010.

International Search Report and Written Opinion for Application No. PCT/US2016/054112, dated Dec. 20, 2016, 13 pages.

Extended European Search Report issued for EP Application No. 16852453.6 dated Apr. 23, 2019 and dated Apr. 30, 2019, The Hague, 3 pages.

* cited by examiner

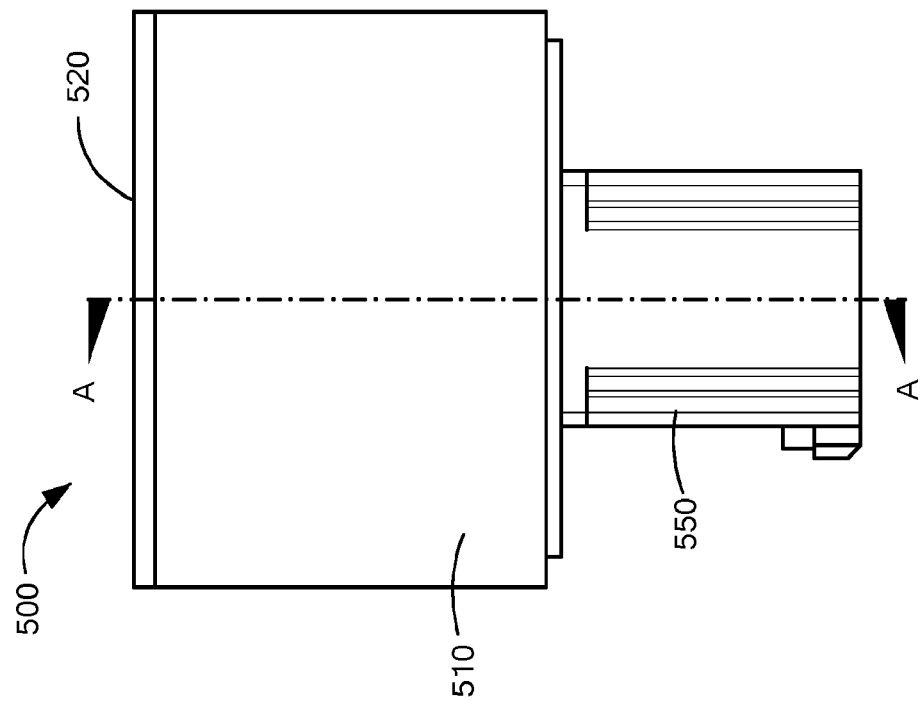
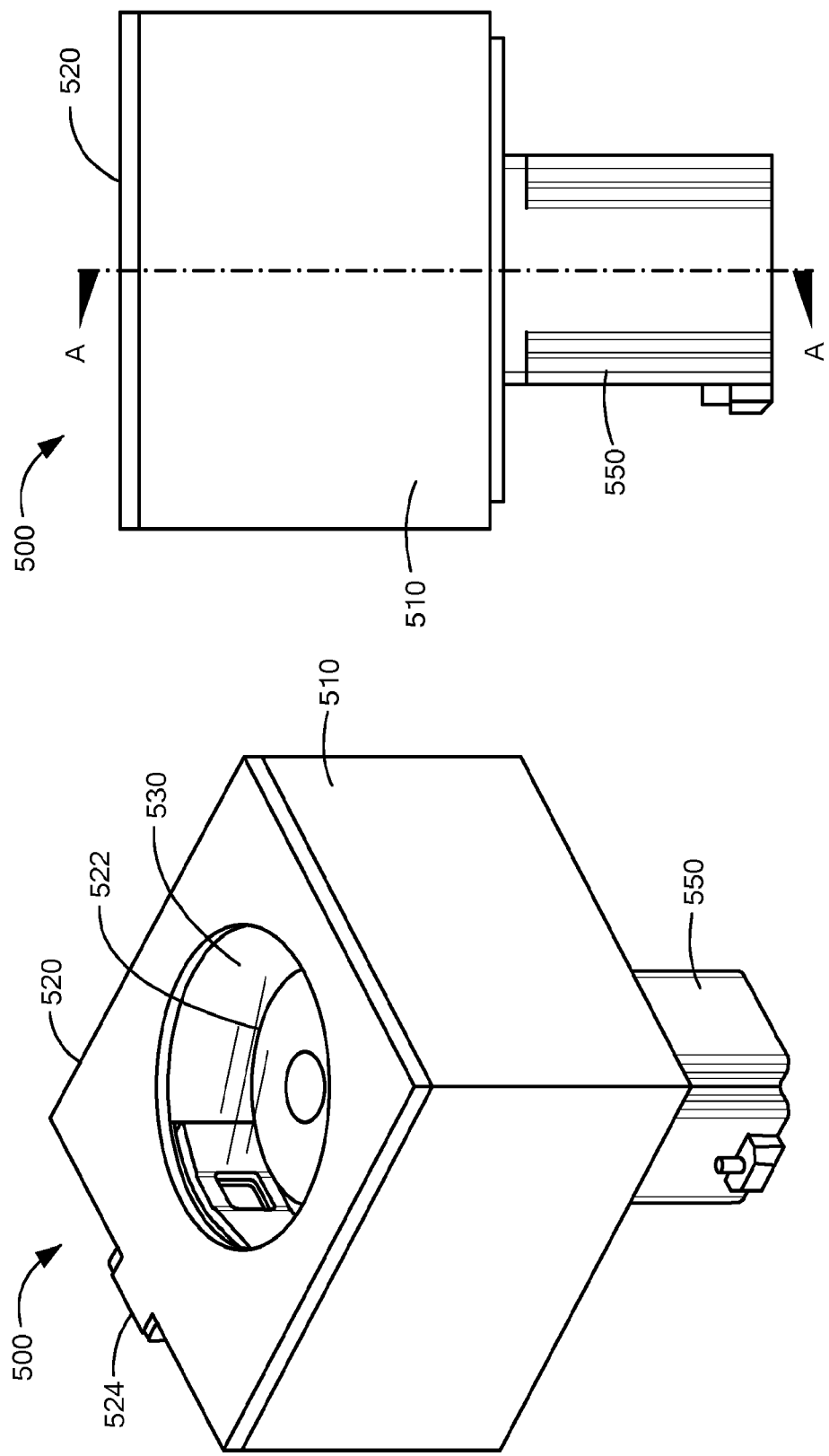
Figure 8B
Figure 8A

SYSTEM AND METHOD FOR IMAGING A ROTATING OBJECT

PRIORITY

This patent application claims priority Application 62/234,188, filed Sep. 29, 2015, entitled "Blood Component Separation Device with Imaging System," and naming Gary Stacey and James Sullivan as inventors, the disclosure of which is incorporated herein, in its entirety by reference.

This patent application also claims priority from U.S. Provisional Patent Application No. 62/302,996, filed Mar. 3, 2016, entitled, "System and Method For Imaging a Rotating Object," and naming Gary Stacey and James Sullivan as inventors, the disclosure of which is incorporated herein, in its entirety, by reference.

TECHNICAL FIELD

The present invention relates to imaging systems, and more particularly to an imaging system for imaging a rotating object.

BACKGROUND ART

When imaging an object it is important to keep the target object in focus in order to obtain a clear image and, if needed, extract the best possible data from the images. A clear image and good image data can be obtained by carefully positioning the optical sensor and lenses used to take the image, and the light source used to illuminate the object. In many prior art systems, if the imaging device views the object from an angle, the extremes/edges of the image may be distorted and/or out of focus which results in poor image quality and poor image data. Therefore, in prior art systems, there are constraints on the positioning of the image/optical sensor. This, in turn, can result in restrictions on overall system size.

Further complications can arise if the object to be imaged is rotating. For example, in the field of blood processing and apheresis, the use of prior art imaging systems can be problematic. Apheresis is a procedure in which individual blood components can be separated and collected from whole blood temporarily withdrawn from a subject. Typically, whole blood is withdrawn through a needle inserted into a vein of the subjects arm and into a cell separator, such as a centrifugal bowl. Once the whole blood is separated into its various components, one or more of the components can be removed from the centrifugal bowl. The remaining components can be returned to the subject along with optional compensation fluid to make up for the volume of the removed component. The process of drawing and returning continues until the quantity of the desired component has been collected, at which point the process is stopped. A central feature of apheresis systems is that the processed but unwanted components are returned to the donor. Separated blood components may include, for example, a high density component such as red blood cells, an intermediate density component such as platelets or white blood cells, and a lower density component such as plasma.

During the apheresis procedure, the operator or technician monitors the procedure in order to ensure that there are no issues with the procedure(s). For example, in addition to monitoring the flowrates, volumes, and pressures within the system, the operator/technician may also rely on sight, sound and touch to confirm that the whole blood is separating properly, and the system is operating properly. However, traditional imaging systems are problematic if attempting to obtain images of the rotating cell separator/centrifuge bowl. Similar problems arise in areas outside of apheresis procedures as well (e.g., when imaging other rotating objects).

SUMMARY OF THE INVENTION

In accordance with one embodiment of the invention, an imaging system for a blood processing device includes an imaging unit, a light source, and a synchronizer. The imaging unit may be configured to take a series of images of at least a portion of a blood component separation device that, in turn, may be configured to rotate about an axis and separate whole blood into a plurality of blood components. The light source may be directed at the blood component separation device, and may be configured to generate pulses of light that illuminate the blood component separation device during rotation. This, in turn, allows the imaging unit to take the series of images of the blood component separation device. The synchronizer (e.g., an angular encoder located on a shaft of the separation device) may be configured to monitor the rotational position of the blood component separation device.

The imaging system may also include a controller that is in communication with the imaging unit, the light source(s), and the synchronizer. The controller may be configured to control the operation of the imaging unit and/or the light source(s) based upon the rotational position of the blood component separation device. By controlling the operation of the imaging unit and/or light source(s), each of the series of images may be taken at the same rotational position of the blood component separation device. The series of images may be displayed on a visual display, may be jitter free, and may include a visual representation of an interface between at least two of the plurality of blood components. The controller may be further configured to control the operation of the blood processing device based, at least in part, on the location of the interface between at least two of the plurality of blood components.

In some embodiments, the imaging unit may be a solid state imager and/or include a CMOS sensor. Additionally or alternatively, the imaging unit may include a lens and an image sensor. The lens and/or the image sensor may be oriented at an angle with respect to the portion of the blood component separation device being imaged. The lens may define a lens plane, and the image sensor may define an image plane. The lens plane may not be parallel to the image plane. In other embodiments, the lens, image sensor, and the portion of the blood component separation device being imaged may be oriented and positioned according to the Scheimpflug principle.

The imaging unit may be configured to read information contained on the blood component separation device. For example, the information may be manufacturer information, a model number, a part number, a manufacture date, outdate information, expiration date information, and/or inspection information. The light source may include a plurality of light emitting diodes having various colors, and the color of the generated pulse of light may be based, at least in part, upon a characteristic of the whole blood to be processed or a characteristic of at least one of the plurality of blood components.

In further embodiments, the imaging system may include a microphone (e.g., a MEMS microphone) configured to pick up the sound of the blood component separation device during rotation and generate and audio output representative of the sound. The controller may be in electrical communication with the microphone and may be configured to receive the audio output and control the operation of the blood processing device based upon the audio output. Additionally or alternatively, the controller may analyze the audio output over a period of time, and determine a performance trend.

Furthermore, some embodiments of the imaging system may include a vibration sensor (e.g., a multi-axis accelerometer) configured to measure the vibration of the blood component separation device during rotation and generate a vibration output representative of the vibration. The controller may be in electrical communication with the vibration sensor and may be configured to receive the vibration output and control the operation of the blood processing device based upon the vibration output. Additionally or alternatively, the controller may analyze the vibration output over a period of time, and determine a performance trend.

In accordance with further embodiments, a blood processing system may include a blood component separation device, an imaging system, a synchronizer, and a controller. The blood component separation device may be configured to rotate about an axis and separate whole blood into a plurality of blood components. The imaging system may include (1) an imaging unit configured to take a series of images of at least a portion of the blood component separation device, and (2) a light source directed at the blood component separation device and configured to generate pulses of light that illuminate (e.g., stroboscopically) the at least a portion of the blood component separation device during rotation (e.g., to allow the imaging unit to take the series of images). The synchronizer may be configured to monitor a rotational position of the blood component separation device. The controller may be in communication with the imaging unit, the light source(s), and the synchronizer. Also, the controller may be configured to control the operation of the imaging unit and/or the light source(s) based upon the rotational position of the blood component separation device such that each of the series of images is taken at the same rotational position of the blood component separation device.

In accordance with additional embodiments, a method of performing a quality check on a blood processing system includes installing a blood component separation device into the blood processing system, rotating the blood component separation device about an axis, and monitoring the rotational position of the blood component separation device as it rotates. The method may also pulse a light source to illuminate at least a portion of the blood component separation device, and take first and second images of the blood component separation device as it rotates. The method may take the first image at a first rotational position of the blood component separation device and when the blood component separation device is illuminated by the light source. The method may take the second image at a second rotational position and when the blood component separation device is illuminated by the light source. The method may then analyze the first and second images to determine whether the blood component separation device is properly aligned.

In some embodiments, analyzing the first and second images may include comparing the radial and/or vertical position of the blood component separation device in the first image with the radial and/or vertical position of the blood component separation device in the second image. If the blood component separation device is not properly aligned, the method may stop the rotation of the blood component separation device and/or indicate (on a display of the blood processing system) that the blood component separation device is not properly aligned.

In accordance with further embodiments, an imaging system for a rotatable object includes an imaging unit, a light source, a synchronizer, and a controller. The imaging unit may be configured to take a series of images of a portion of the rotatable object, and the rotatable object may rotate about an axis. The light source may be directed at the rotatable object and may be configured to generate pulses of light that illuminate a portion of the rotatable object during rotation. The illumination allows the imaging unit to take the series of images of the rotatable object. The synchronizer may monitor the rotational position of rotatable object as it rotates. The controller may be in communication with the imaging unit, the light source, and the synchronizer and may control the operation of the imaging unit and/or the light source based upon the rotational position of the rotatable object such that each of the series of images is taken at the same rotational position of the rotatable object.

The light source may be a monochromatic light source and/or a wide band light source. If the light source is a wide band light source, the imaging system may also include a monochromator that selectively separates a predetermined wavelength of light from the wide band light source. The light source may include a microlens diffuser configured to diffuse the light generated by the light source. The imaging unit may be off-set from the axis of rotation of the rotatable object.

In some embodiments, the imaging unit may include a lens and an image sensor. The lens and/or the image sensor may be oriented at an angle with respect to the portion of the rotatable object (e.g., the portion being imaged). The lens may define a lens plane and the image sensor may define an image plane. The lens plane may not be parallel to the image plane. The lens (e.g., a wide angle lens), image sensor, and the at least a portion of the rotatable object may be oriented and positioned according to the Scheimpflug principle. Additionally or alternatively, the lens may be a scanning variable focus lens that scans across a top surface of the rotatable object. In such embodiments, the image sensor may capture a plurality of images of the top surface of the rotatable object as the scanning variable focus lens scans, and the controller may stitch together the plurality of images of the top surface to obtain an image of the top surface of the rotatable object.

In additional embodiments, the imaging system may include a mirror located above a top surface of the rotatable object. The mirror may generate a reflection of at least a portion of the rotatable object. The imaging unit may be focused on the mirror such that the series of images of the rotatable object includes a series of images of the reflection. The mirror may be a MEMS mirror. The controller may be in communication with the MEMS mirror and may adjust the MEMS mirror to cause the MEMS mirror to scan across the at least a portion of the rotatable object.

In some embodiments, the rotatable object may be a blood processing device that includes one or more chambers configured to hold one or more blood storage containers. In such embodiments, the imaging unit may take a series of images of the one or more blood storage containers, and the controller may determine a level of blood separation within the one or more blood storage containers. Additionally or alternatively, the rotatable object may be configured to hold one or more fluid samples, and the imaging unit may take a series of images of the one or more fluid samples. For example, the fluid samples may be reagents, and the controller may determine a level of agglutination.

In other embodiments, the rotatable object may include a plurality of parts located on a surface of the rotatable object. In such embodiments, the imaging unit may take images of each of the plurality of parts. Also, the controller may determine one or more measurements of each of the plurality of parts based on the images. Additionally or alternatively, the controller may determine a level of uniformity between the plurality of parts based on the one or more measurements.

The imaging system may include (1) an enclosure having a chamber within an interior of the enclosure and (2) a lid configured to selectively close the enclosure. The rotatable object may be located within the chamber during rotation. The lid may include a window and/or a support structure. The support structure may extend downward from the lid toward the rotatable object to support the rotatable object as the object rotates. The system may also include (1) a turntable configured to support the chamber, (2) a motor configured to rotate the turntable and the rotatable object, (3) a drive shaft operably coupling the motor and the turntable, and/or (4) a bottom plate located below and secured to the chamber. The bottom plate may have an opening and the drive shaft may extend through the opening.

In accordance with further embodiments, a method of imaging a rotating object includes (1) rotating an object about an axis, (2) monitoring the rotational position of the object as it rotates, (3) pulsing a light source to illuminate at least a portion of the rotating object, (4) taking a first and second image of the rotating object as the rotating object rotates, and (5) analyzing the first and second images to determine at least one characteristic of the rotating object. The first image may be taken at a first rotational position of the rotating object and when a portion of the rotating object is illuminated by the light source. The second image may be taken at a second rotational position and when the rotating object is illuminated by the light source. The light source may be a monochromatic light source and/or a wide band light source. The light source may include a monochromator that selectively separates a predetermined wavelength of light from the light source (e.g., from the wide band light source).

The first and second images may be taken via an imaging unit that is off-set from the axis of rotation of the rotating object. The imaging unit may include a lens and an image sensor. The lens and/or the image sensor may be oriented at an angle with respect to at least a portion of the rotating object. Also, the lens may define a lens plane and the image sensor may define an image plane. The lens plane may not be parallel to the image plane. The lens, image sensor, and the at least a portion of the rotating object may be oriented and positioned according to the Scheimpflug principle.

The lens may be a scanning variable focus lens that is configured to scan across a top surface of the rotating object. The method may further take a plurality of images of the top surface of the rotating object and stitch together the plurality of images of the top surface to obtain an image of the top surface of the rotating object. Additionally or alternatively, the lens may be a wide angle lens.

In some embodiments, taking the first and second images may include taking first and second images of a reflection generated by a mirror located above the top surface of the rotating object. The mirror may be a MEMS mirror, and the method may further include adjusting the MEMS mirror to cause the MEMS mirror to scan across a portion of the rotating object.

The rotating object may be a blood processing device and may include one or more chambers configured to hold one or more blood storage containers. In such embodiments, the method may include taking images of the one or more blood storage containers, and the at least one characteristic of the rotating body may include a level of blood separation within the blood storage containers. Alternatively, the rotating object may be configured to hold one or more fluid samples, and the first and second images may be images of the one or more fluid samples. For example, the fluid samples may be reagents, and the at least one characteristic may be a level of agglutination within each of the fluid samples.

The rotating object may also include a plurality of parts located on a surface of the rotating object, and taking the first and second images may include taking images of each of the plurality of parts. In such embodiments, the method may analyze the images of the plurality of parts, and the at least one characteristic may be one or more measurements of the plurality of parts (e.g., based on the images of the each of the plurality of parts). Additionally or alternatively, the at least one characteristic may include a level of uniformity between the plurality of parts based on the one or more measurements.

BRIEF DESCRIPTION OF THE DRAWINGS

The foregoing features of the invention will be more readily understood by reference to the following detailed description, taken with reference to the accompanying drawings, in which:

FIGS. 8A and 8B schematically show perspective and side views of an alternative imaging system, in accordance with an additional embodiment of the present invention.

DETAILED DESCRIPTION OF SPECIFIC EMBODIMENTS

Illustrative embodiments of the present invention provide a system, and blood component separation device for performing a blood apheresis procedure. Additionally, various embodiments of the present invention image a portion of the blood processing device to monitor the separation of whole blood and the locations of the interfaces between the separated blood components within the separation device.

Figure 1:
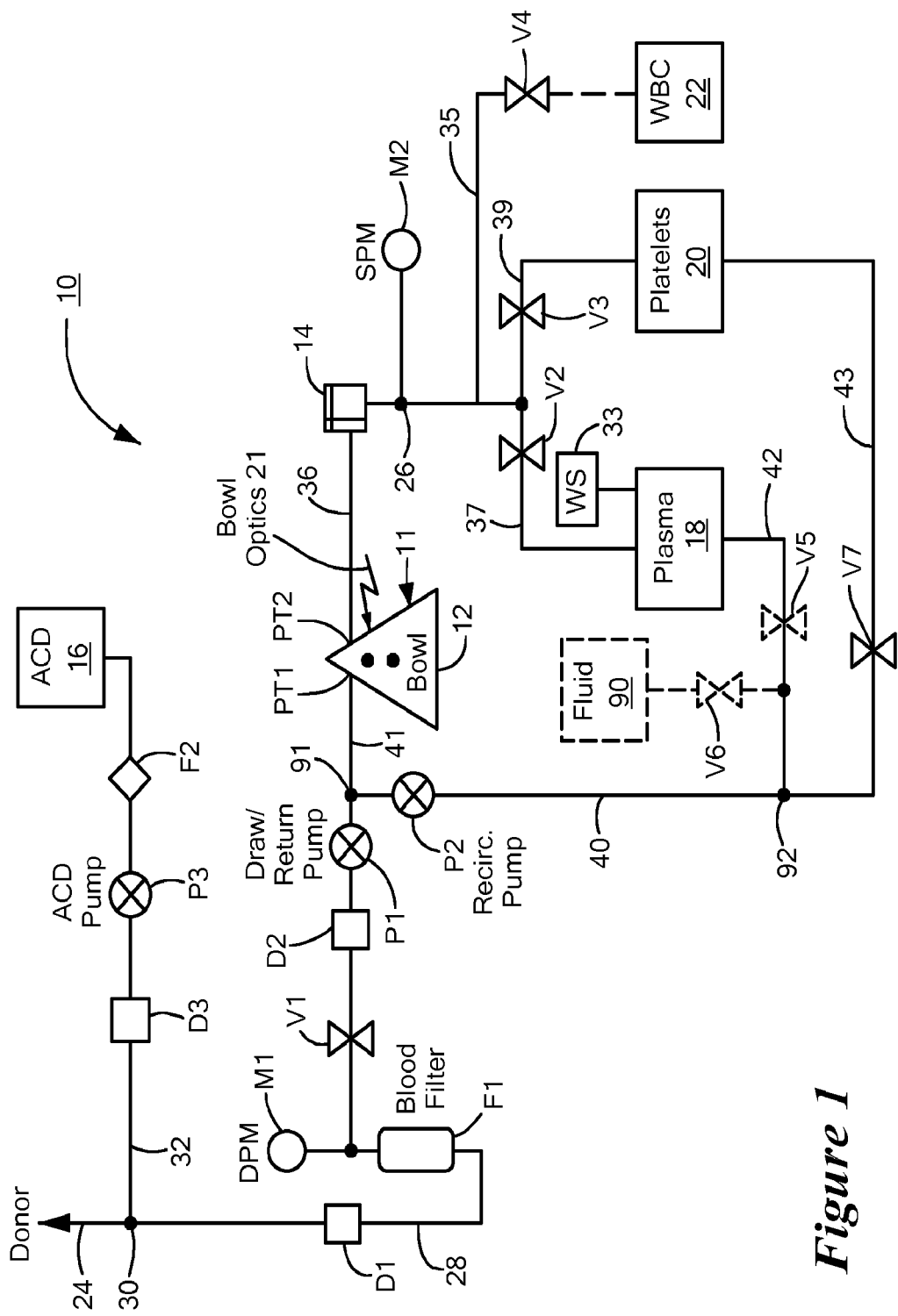
FIG. 1 shows a schematic diagram of an apheresis system in accordance with embodiments of the present invention.
Figure 2:
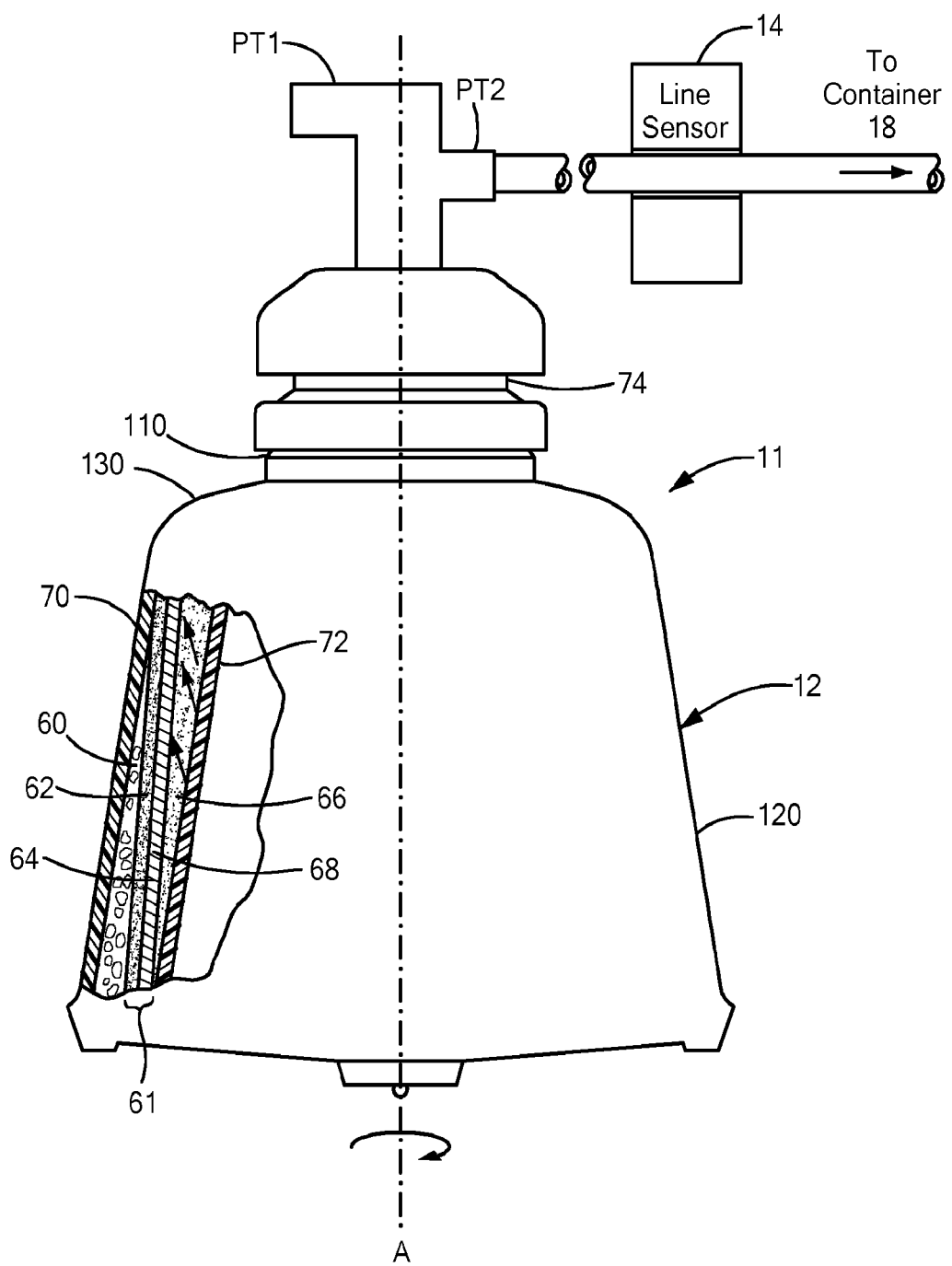
FIG. 2 schematically shows a side view of a blood component separation device for use with the apheresis system of FIG. 1, in accordance with embodiments of the present invention.

As shown in FIGS. 1 and 2, and as mentioned above, an apheresis system 10, in accordance with embodiments of the present invention, withdraws whole blood from a subject through a venous access device 24 using a withdraw pump P1. The venous access device 24 can be any number of devices capable of accessing a subject's veins including, but not limited to a phlebotomy needle. As the system 10 withdraws the whole blood from the subject, the blood passes through a draw/return line 28 and enters a blood component separation device 11, such as a Latham type centrifuge. The blood component separation device 11 separates the whole blood into its constituent components (e.g., red blood cells, white blood cell, plasma, and platelets). Although a Latham type centrifuge is mentioned above, other types of separation chambers and devices may be used, such as, without limitation, an integral blow-molded centrifuge bowl, as described in U.S. Pat. Nos. 4,983,156 and 4,943,273, which are hereby incorporated by reference.

As the system 10 withdraws the whole blood from the subject, the system 10 may introduce anticoagulant into the withdrawn whole blood to prevent the blood from coagulating within the lines or within the blood component separation device 11. To that end, the system 10 may include an anticoagulant line 32 fluidly connected to an anticoagulant source 16 (e.g., a bag of anticoagulant) at one end, and the venous-access device 24 (or the draw/return line 28 via a y-connector 30) at the other end. An anticoagulant pump P3, through which the anticoagulant line 32 passes, may control the flow of anticoagulant within the anti-coagulant line 32 and the amount of anticoagulant introduced into the whole blood. Although the anticoagulant can be added to the whole blood at any point, it is preferred that the anticoagulant be introduced as close as possible to the venous-access device 24.

The anticoagulant line 32 may also include a bacteria filter F2 that prevents any bacteria in the anticoagulant source 16, the anticoagulant, or the anticoagulant line 32 from entering the system 10 and/or the subject. Additionally, the anticoagulant line 32 may include an air detector D3 that detects the presence of air within the anticoagulant. The presence of air bubbles within any of the system 10 lines can be problematic for the operation the system 10 and may also be harmful to the subject if the air bubbles enter the blood stream. Therefore, the air detector D3 may be connected to an interlock that stops the flow within the anticoagulant line 32 in the event that an air bubble is detected (e.g., by stopping the anticoagulant pump P3 or closing a valve on the anticoagulant line 32), thereby preventing the air bubbles from entering the subject.

Once a desired amount of anti-coagulated whole blood is withdrawn from the subject and contained within the blood component separation device 11, the blood component separation device 11 separates the whole blood into several blood components. For example, the blood component separation device 11 may separate the whole blood into a first, second, third, and, perhaps, fourth blood component. More specifically, the blood component separation device 150 can separate the whole blood into plasma, platelets, red blood cells, and, perhaps, white blood cells.

As shown in FIG. 2, when a Latham centrifuge is used, the blood component separation device 11 includes a rotatable bowl 12 and stationary input and output ports PT1 and PT2 fluidly coupled to the bowl interior by a rotary seal 74. The rotatable bowl may include a neck portion 110 coupled to the rotary seal 74, and a body portion 120 that defines the interior volume of the separation device (e.g., the interior volume of the rotatable bowl 12). The bowl 12 (e.g., the body portion 120) may have a frustoconical shape. The rotatable bowl 12 may also include a shoulder portion 130 extending between and connecting the neck portion 110 and the body portion 120.

Additionally, some embodiments may have a core 72 that occupies a volume coaxial with the interior of bowl 12 and provides a separation region between the wall of the core 72 and the outer bowl wall 70. The draw/return line 28 fluidly connects the venous access devices 24 (e.g., the phlebotomy needle) and the input port PT1. In some embodiments, the venous access device 24 may be replaced with a whole blood bag (not shown) in case the whole blood is to be first pooled and then supplied. In such embodiments, the draw line 28 will fluidly connect the whole blood bag with the input port PT1.

As mentioned above, the blood component separation device 11 separates the whole blood into its constituent components. In particular, as the bowl 12 rotates, centrifugal forces separate the anticoagulated whole blood admitted into the bottom of the bowl into red blood cells (RBC), white blood cells (WBC), platelets and plasma. The number of rotations of the bowl 12 can be selected, for example, within a range of 4,000 to 6,000 rpm, and is typically 4,800 rpm. The blood is separated into different fractions in accordance with the component densities. The higher density component, i.e., RBC 60, is forced to the outer wall 70 of the bowl 12 while the lower density plasma 66 lies nearer the core 72. A buffy coat 61 is formed between the plasma 66 and the RBC 60. The buffy coat 61 is made up of an inner layer of platelets 64, a transitional layer 68 of platelets and WBC and an outer layer of WBC 62. The plasma 66 is the component closest to the outlet port from the separation region and is the first fluid component displaced from the bowl 12 via the outlet port PT2 as additional anticoagulated whole blood enters the bowl 12 through the inlet port PT1.

The system 10 may also include an optical sensor 21 (FIG. 1) that may be applied to the shoulder portion 130 of the bowl 12. The optical sensor 21 monitors each layer of the blood components as they gradually and coaxially advance toward the core 72 from the outer wall 70 of the bowl 12. The optical sensor 21 may be mounted in a position at which it can detect the buffy coat reaching a particular radius, and the steps of drawing the whole blood from the subject/donor and introducing the whole blood into the bowl 12 may be terminated in response to the detection.

Once the blood component separation device 11 has separated the blood into the various components, one or more of the components can be removed from the blood component separation device 11. For instance, the plasma may be removed to a plasma bag 18 through line 37 (FIG. 1) or a waste bag (not shown). Alternatively, the plasma may be removed to a plasma reservoir (not shown) located on the draw/return line 28, or the white blood cells (WBC) may be removed to one or more white blood cell bags 22 via line 35. Some embodiments of the system 10 may include a weight sensor 33 that measures the amount plasma collected. Although not shown, the platelet bag 20 and the white blood cell bag 22 may include similar weight sensors. The removed plasma may be later reintroduced into the blood component separation device 11 via line 40 and recirculation pump P2 at an increasing rate to extract and send the platelets to a platelet bag 20 via line 39. This process is known as surge elutriation.

In some embodiments, the system 10 may also include a line sensor 14 that can determine the type of fluid (e.g., plasma, platelets, red blood cells etc.) exiting the blood component separation device. In particular, the line sensor 14 consists of an LED which emits light through the blood components leaving the bowl 12 and a photo detector which receives the light after it passes through the components. The amount of light received by the photo detector is correlated to the density of the fluid passing through the line. For example, if plasma is exiting the bowl 12, the line sensor 14 will be able to detect when the plasma exiting the bowl 12 becomes cloudy with platelets (e.g., the fluid exiting the bowl 12 is changing from plasma to platelets). The system 10 may then use this information to either stop the removal of blood components from the bowl 12 or redirect the flow by, for example, closing valve V2 and opening valve V3.

Once the system removes the desired components from the blood component separation device 11, the system 10 can return the remaining components to the subject. The system may use the draw/return pump P1 to return the components to the subject via the draw/return line 28, which, as mentioned above, fluidly connects the blood component separation device 11 and the venous-access device 24. Alternatively, if the system 11 is so equipped, the system may return the components to the subject via a dedicated return line. Like the anticoagulant line 32 and the draw/return line 28, the dedicated return line may also have a dedicated return pump that controls the direction, rate, and duration of the fluid flow within the return line. In such embodiments, the return line also fluidly connects to the venous-access device 24, preferably at a point between the return pump and the venous-access device 24. Additionally, in such embodiments, the system 10 will also have a dedicated draw line and draw pump. In some embodiments, the system 10 may include an interlock that stops the withdrawal of whole blood from the subject when the system is returning the first blood component to the subject.

As shown in FIG. 1 and as mentioned briefly above, the system 10 can have a plurality of valves located throughout the system to control the flow of fluid within the system 10. For example, draw/return line 28 may contain a valve V1 that allows flow through the lines when open and prevents flow when closed. Additionally, the lines 35, 37 and 39 leading to the white blood cell, plasma and platelet bags, respectively may have at least one valve V2, V3, V4, and V5 (e.g., line 37 has a valve V2 at the inlet of the plasma bag 18 and a valve V5 at the outlet of the plasma bag 18, and line 39 has a valve V3 at the inlet of the platelet bag 20). Additionally, the inlet to the blood component separation device 11 may have valves (not shown) that either allow or prevent flow to or from the blood component separation device 11. Any of the above mentioned valves can be either manual or automatic. In other words, the valves may be manually operated by the user/technician or can be automatically operated, for example, by a controller, when a particular condition is met (e.g., closing valve V1 when air is detected in the draw/return line 28, as discussed below).

Like the anticoagulant line 32, the draw/return line 28 can also include a number of sensors, filters, and detectors to ensure the safety of the subject and an optimized system operation. In particular, as shown in FIG. 1, the draw/return line 28 may include air detectors D1 and D2 to detect the presence (or absence) of air within the line 28. The air detectors D1 and D2 can be connected to an interlock that, when the detectors D1 and D2 detect air, stops flow within the draw/return line 28 (e.g., by stopping the draw/return pump P1 or closing valve V1). Additionally, the draw line 28 can include a blood filter F1 that removes any bacteria, contamination, or particulates that may be present in the withdrawn blood or the returning components.

Figure 3:
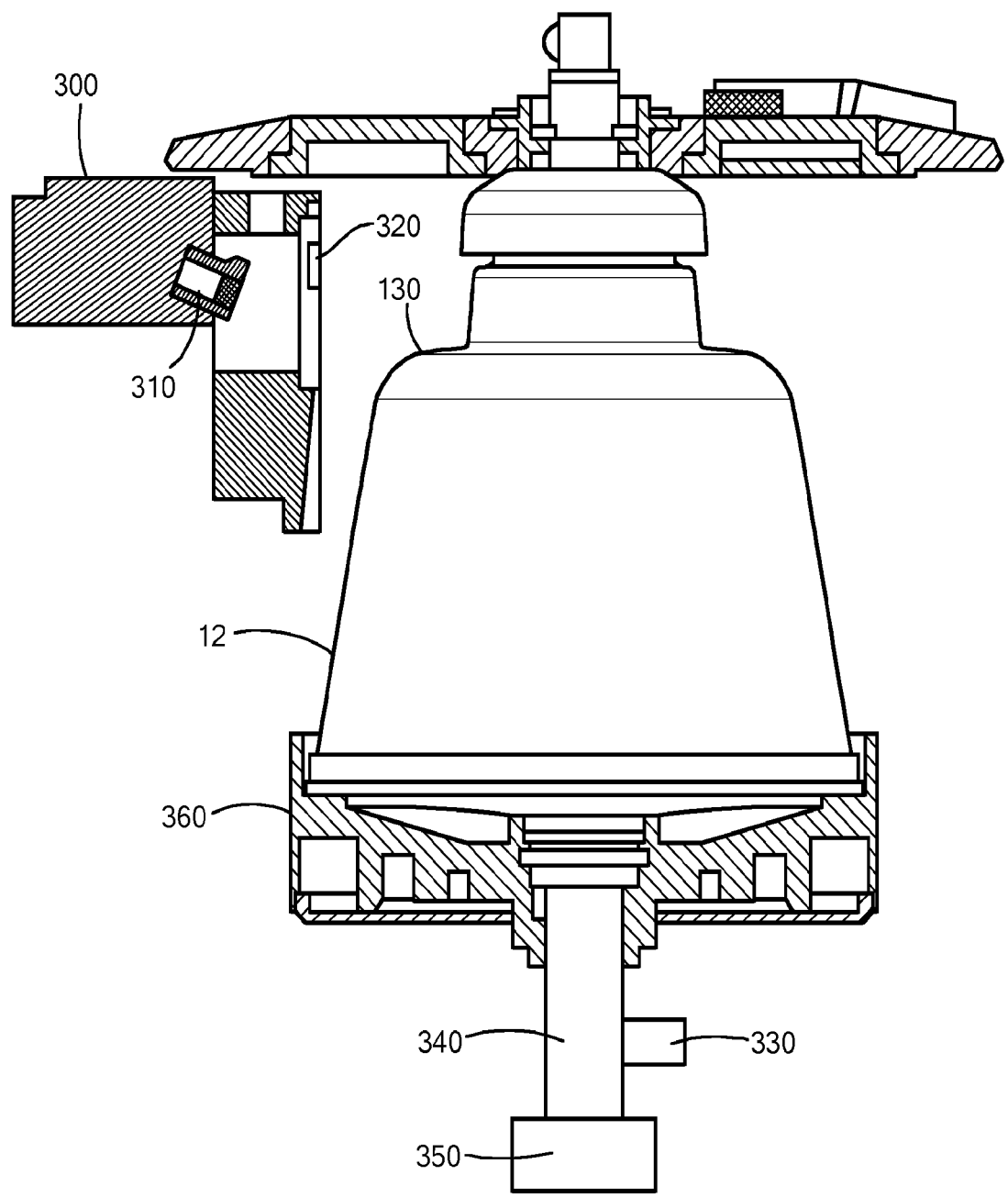
FIG. 3 schematically shows an imaging system for the apheresis system shown in FIG. 1, in accordance with embodiments of the present invention.

As mentioned above, during operation and blood processing, it is important to monitor the separation of the whole blood into its individual components (e.g., red blood cells, platelets, plasma). To that end, as shown in FIG. 3, some embodiments of the present invention may include an imaging system 300 that takes images and/or video of a portion of the blood component separation device 11 (e.g., the shoulder 130 of the bowl 12). The imaging system 300 may include an imaging unit 310 and a light source 320 that, as discussed in greater detail below, illuminates an area on the blood component separation device 11 to be imaged.

In some embodiments, the imaging unit 310 may be a wide band monochromatic solid state imager, and/or may include one or more cameras (e.g., 2-8 cameras) aimed at the top of the blood component separation device 11. For example, the imaging unit 310 may be aimed at the shoulder 130 of the separation device 11/bowl 12 such that the imaging unit 310 may take images (or video) of the shoulder 130. This, in turn, allows the imaging unit 310 to take images/video of the blood separation taking place within the separation device 11/bowl 12 (e.g., the imaging unit 310 may take images/video of the various blood components within the separation device 11 and the interfaces between each of the blood components). As discussed in greater detail below, the imaging unit 310 may also include a lens 312 and image sensor 314 (e.g., a CMOS sensor array).

It is important to note that, in some instances, imaging a large portion of the separation device 11 (e.g., the entire top/shoulder 12 of the separation device 11/bowl 12) may be impractical with conventional optics (e.g., conventional lenses and conventional lens configuration) because of the size restrictions associated with the blood processing/ apheresis system 10. For example, the size of the blood processing system 10 limits the maximum possible distance from the shoulder 130 of the separation device 11/bowl 12 to the imaging unit 310, and this distance does not provide an adequate depth of field, meaning only a very limited amount of the separation device 11 would be in focus. Therefore, in some embodiments, the imaging unit 310 may be oriented/configured according to the Scheimpflug principle.

Figure 4:
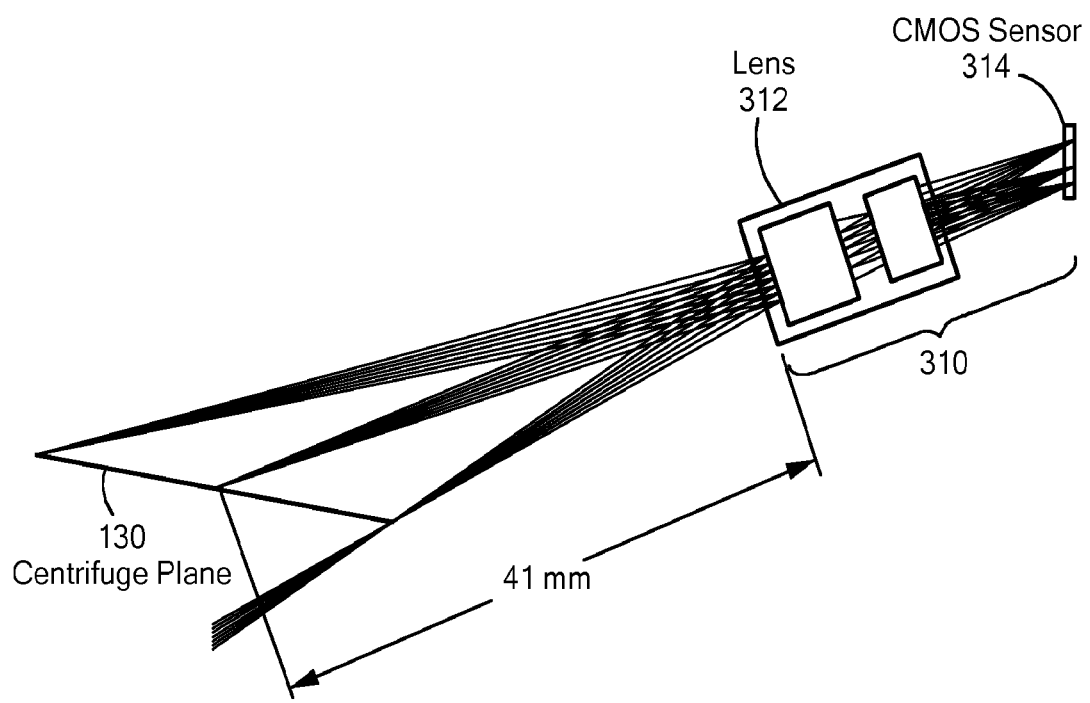
FIG. 4 schematically shows an exemplary layout of the imaging system with respect to the blood component separation device, in accordance with embodiments of the present invention.
Figure 5:
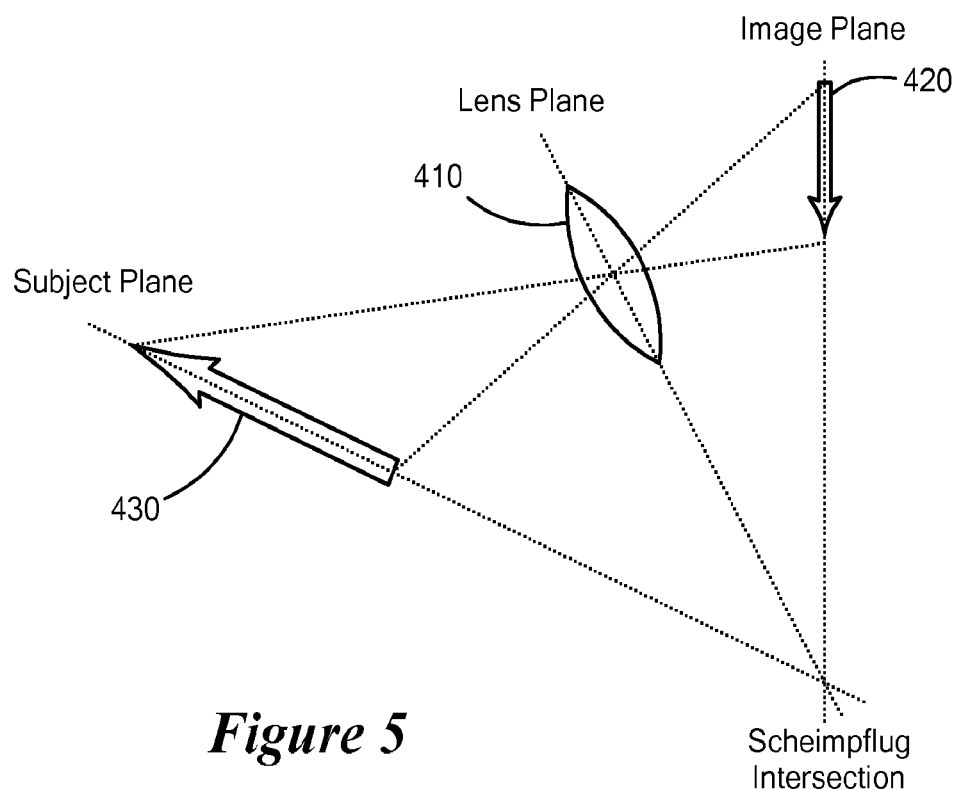
FIG. 5 schematically shows a layout of a lens and imaging unit according to the Scheimpflug principal, in accordance with additional embodiments of the present invention.

For example, as shown in FIGS. 4 and 5, the imaging unit 310 may be oriented/configured such that the lens 312 is at an angle with respect to the shoulder 130 of the separation device 11/bowl 12, and the image sensor 314 is substantially vertical (see FIG. 4). By orienting the lens 312 and image sensor 314 in this manner, the lens plane 410 and the image plane 420 (FIG. 5) have similar orientations with respect to the shoulder 130 of the separation device 11 (e.g., the subject plane 430). In other words, as shown in FIG. 5, the lens plane 410 may be at an angle with respect to the shoulder 130/subject plane 430 and the image plane 420 may be substantially vertical. This, in turn, allows the shoulder 130 of the separation device (e.g., the subject plane 430) to be in focus even though it is not parallel to the image sensor 314/image plane 420. Such a configuration reduces the required distance between the imaging unit 310 and the separation device 11/bowl 12.

The light source 320 may include one or more light emitting diodes (LEDs) that pulse to illuminate the shoulder 130 of the separation device 11. In some embodiments, the light source 320 may include an array of LEDS having varying colors (e.g., red, green, blue, etc.) to allow the imaging system 300 to illuminate the shoulder 130 of the separation device 11 in a number of colors. Additionally or alternatively, the LEDs may be integrated with the image sensor 314 (e.g., the LEDs may be integrated with the CMOS array). As discussed in greater detail below, by having multiple colors, the imaging system 300 and blood processing system 10 may further analyze the quality of separation, the purity of the separated components, and identify various donor anomalies (e.g., lipemia, red cell spillage, etc.).

In many applications, it may be important to take and/or record the images at precise positions as the separation device 11 rotates. To that end, some embodiments of the present invention (e.g., as shown in FIG. 3) may have a synchronizer 330 (e.g., an angular encoder) located on the shaft 340 (e.g., the drive shaft) extending between and mechanically coupling the motor 350 and the chuck 360 in which the bowl 12 may be installed (e.g., to facilitate spinning of the bowl 12). Additionally or alternatively, if the motor 350 includes an encoder, some embodiments may utilize the encoder within the motor 350 (e.g., the synchronizer/encoder 330 may be located within the motor 350 itself). During use, the synchronizer 330 may monitor the rotation and the rotational position of the separation device 11/bowl 12. As discussed in greater detail below, the imaging system 300 may utilize the rotational position of the separation device 11 to synchronize the imaging and illumination of the separation device 11/bowl 12 with the bowl rotation and rotational position.

In order to control the operation of the imaging system 300 (e.g., in conjunction with the blood processing system 10), the imaging unit 310, the light source 320, and the synchronizer 330 may be in electrical communication with a controller (not shown) that controls the operation of the imaging system 300. For example, the imaging unit 310, the light source 320, and the synchronizer 330 may be in electrical communication with the controller for the blood processing system 10 (discussed above), or a separate controller dedicated to the imaging system 300. The imaging unit 310, the light source 320, and the synchronizer 330 can each send an output to the controller which, as discussed in greater detail below, may be used to control the operation of the imaging system 300.

During use and as the separation device 11/bowl 12 rotates, the synchronizer 330 monitors the rotational position of the separation device 11 and sends an output representative of the rotational position to the controller. Based upon the rotational position output from the synchronizer 330, the controller will control the operation of the imaging unit 310 and the light source 320. For example, the controller may control the exposure of the imaging unit 310 and the pulse of the light source 320 such that the light source pulses/strobes and the imaging unit 310 takes an image at a predetermined rotational position of the separation device 11 (e.g., to generate a stream of images taken at the same rotational position of the bowl 12). In this manner, the imaging system 300 can provide a jitter free image stream of the separation device 11 (e.g., the shoulder 130 of the separation device 11). The images may be displayed on a visual display on the imaging system 300 and/or the blood processing device 10 so that they may be viewed by the operator/technician.

By taking the series of images of the shoulder 130, the imaging system 300 is able to generate an image stream depicting the contents of the separation device 11/bowl 12, and provides information on the blood processing procedure and the quality of separation of the whole blood within the separation device 11. For example, the image stream may clearly show (which allows the controller to precisely detect) the location of the air-plasma interface, the plasma-buffy coat interface, and the buffy coat-red cell interface within the separation device 11/bowl 12. The location of these interfaces, in turn, provides valuable information concerning the efficiency of the blood processing device 10, as well as information regarding the donor. Based upon the location of the interfaces, the operator/technician and/or the controller can determine the separation efficiency, the efficiency of the pumps (e.g., pumps P1, P2, and/or P3), and the donor's hematocrit. Additionally, based upon the dimensions of the buffy coat layer and the spectral information, the operator/technician and/or the controller can determine/obtain information regarding the donor's platelet count.

It is important to note that, based upon the information obtained from the series of images, the controller (e.g., the controller for the imaging system 300 and/or the controller for the blood processing system 10) can control the operation of the various components of the processing system 10. For example, if one or more of the interfaces is not in the proper location, the controller can increase or decrease the speed of the draw/return pump P1 and/or the recirculation pump P2 to adjust the interface location. Additionally or alternatively, much like the optical sensor 21 described above, the series of images obtained from the imaging system 300 may be used to terminate the draw step and/or whole blood introduction step discussed above. In this manner, the imaging system 300 may be used in conjunction with or instead of the optical sensor 21.

As mentioned above, the light source 320 may contain multiple LEDs having varying colors. In such embodiments, the imaging system may start the imaging process using a first color (e.g., green). The imaging system 300 (and/or the controller) may then analyze the images taken by the imaging unit 310 and/or analyze the absorption of the light produced by the LED. If the imaging system 300 detects a problem and/or a donor anomaly (e.g., plasma composition, lipemia, red cell spillage, plasma discoloration, etc.), the system 300 (e.g., the controller) may change the color of the light generated by the light source 320 and used to illuminate the separation device 11/bowl 12. For example, the system 300/controller may change the color from green to red or from green to blue.

Figure 6A:
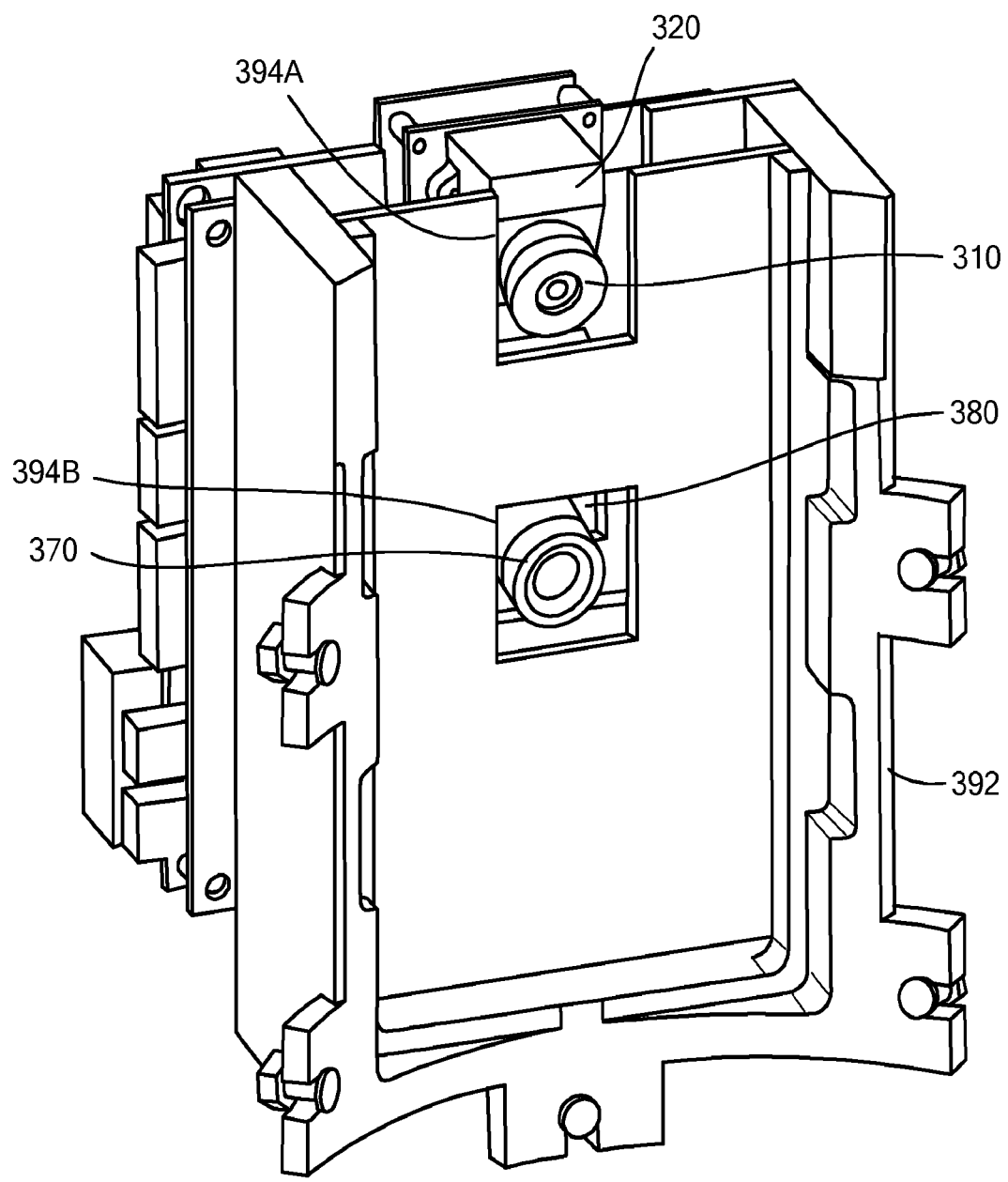
FIGS. 6A-6C schematically show various views of an alternative embodiment of an imaging system for the apheresis shown in FIG. 1, in accordance with additional embodiments of the present invention.
Figure 6B:
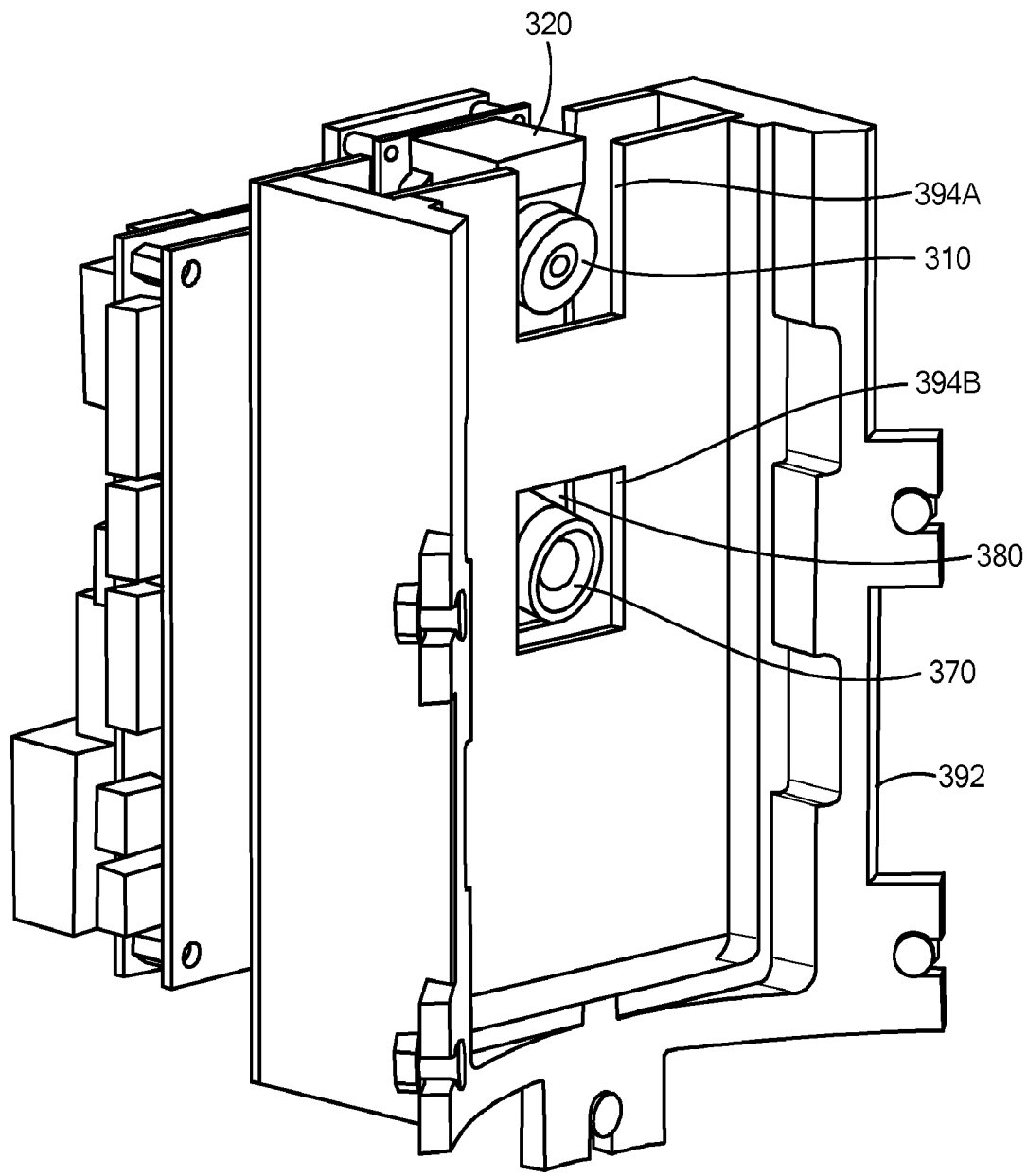
Figure 6C:
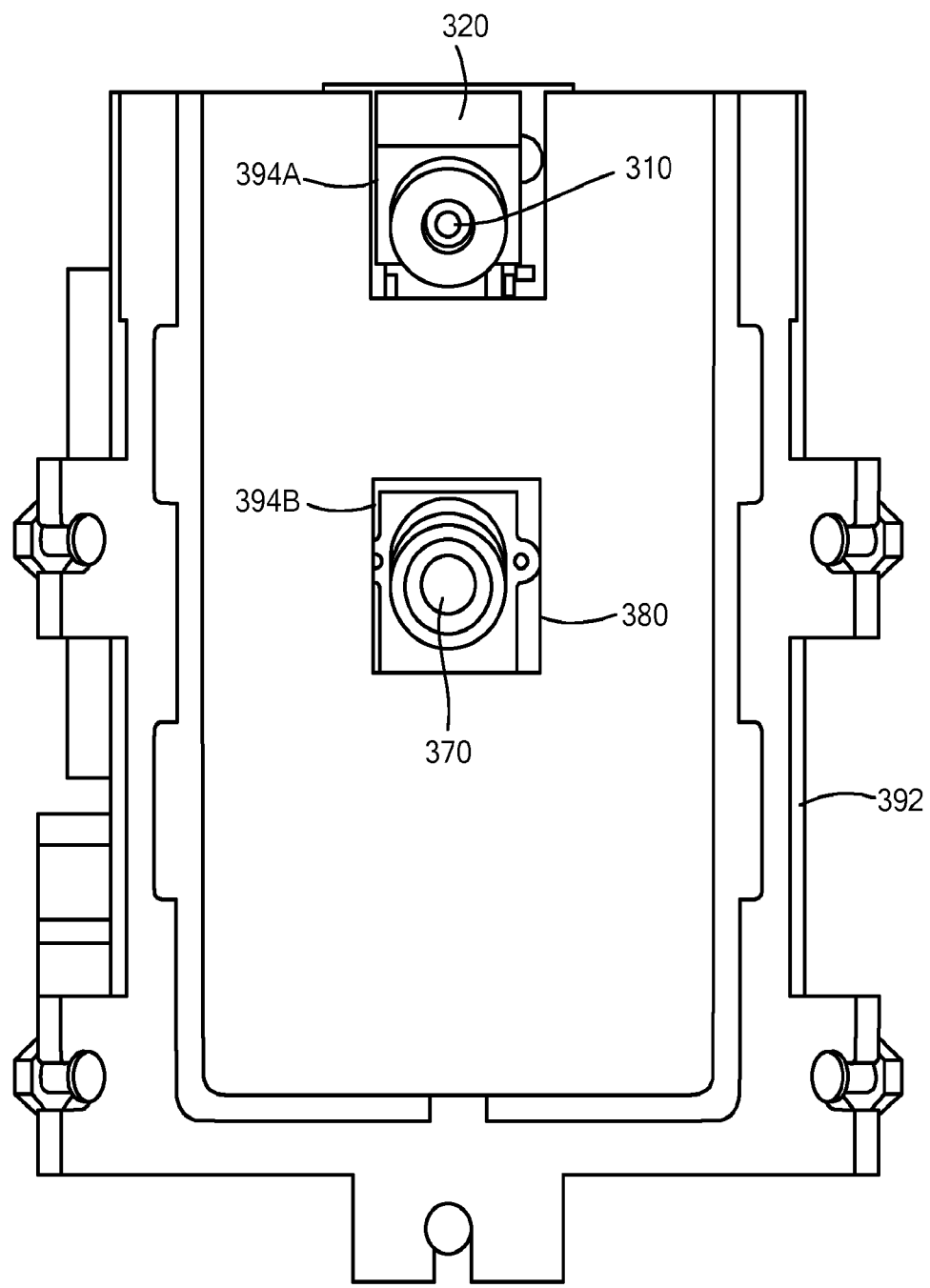

Although the embodiments described above have a single imaging unit 310 aimed at the shoulder portion 130 of the bowl 12, some embodiments may include more than one imaging unit. For example, as shown in FIGS. 6A-6C, the imaging system 300 may include a second imaging unit 370 (e.g., a second camera or series of cameras), in addition to the first imaging unit 310. In such embodiments, the second imaging unit 370 may have a wide angle lens and may be aimed at the body portion 120 of the bowl 12 (e.g., the portion extending between the bottom of the bowl 12 and the shoulder portion 130). This allows the second imaging unit 370 to image the portions of the bowl 12 that the first imaging unit 310 is unable to see.

Like the first imaging unit 310, the second imaging unit may also include a light source 380 with one or more light emitting diodes (LEDs) that pulse to illuminate the bowl 12 (e.g., the body portion 120 of the bowl). In some embodiments, like the light source 320 for the first imaging unit 310, the light source 380 may include an array of LEDS having varying colors (e.g., red, green, blue, etc.) to allow the imaging system 300 to illuminate the body portion 120 of the separation device 11 in a number of colors. Alternatively, the light source 320 for the first imaging unit 310 may be positioned such that it illuminates both the shoulder portion 130 and the body portion 120 of the bowl 12, to allow both the first imaging unit 310 and the second imaging unit 370 to image their respective portions of the bowl 12.

Figure 7A:
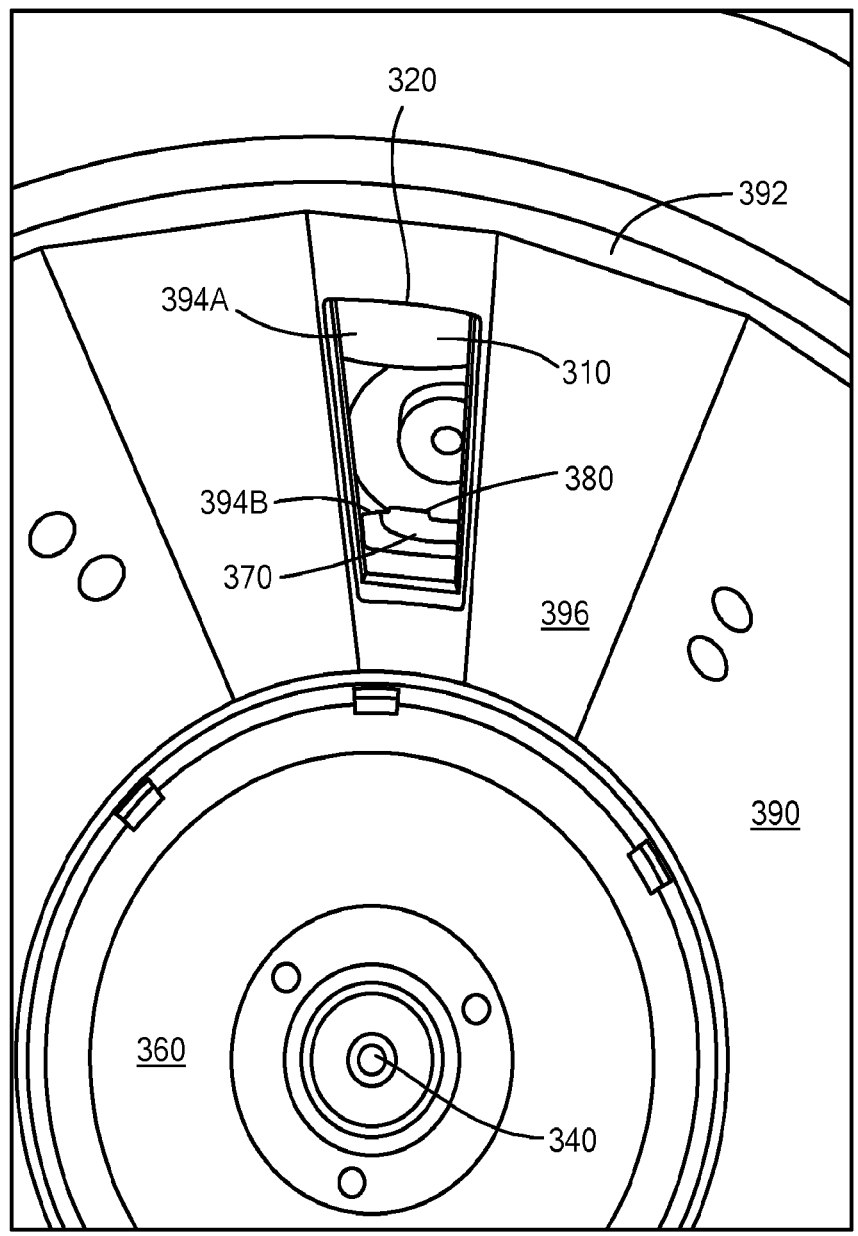
FIGS. 7A and 7B schematically show the alternative imaging system of FIGS. 6A-6C integrated into an apheresis system, in accordance with some embodiments of the present invention.
Figure 7B:
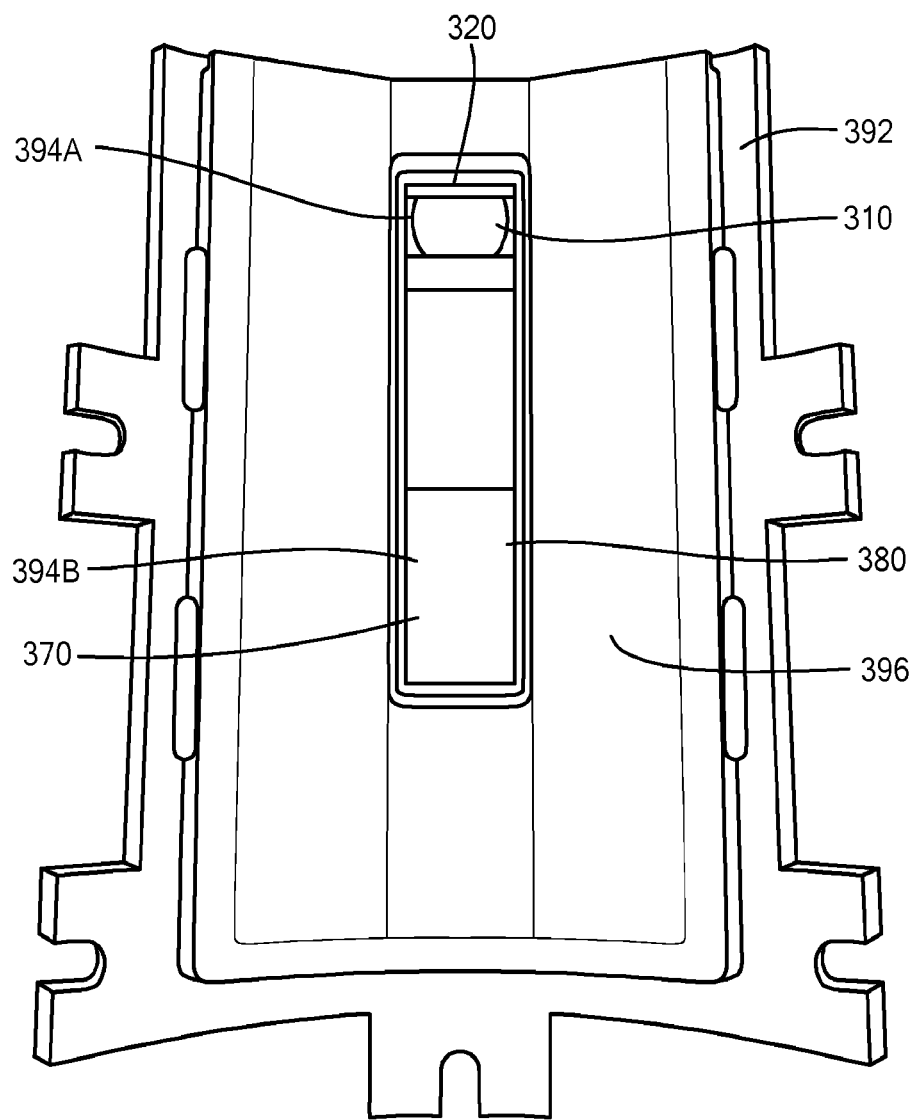

During installation and system set-up, the bowl 12 may be placed within a chuck 360 that holds the bowl 12 in place and rotates to create the centrifugal force required to separate the whole blood. As shown in FIGS. 7A/B, in some embodiments, the first and second imaging units 310/370 may be built into a stationary wall 390 that extends upward from the bottom of the chuck 360 and essentially houses the bowl 12 when installed. For example, as shown in FIGS. 6A-C and 7A/B, a section 392 of the wall 390 can have one or more openings 394A/B through which the imaging units 310/370 can image their respective portions of the bowl 12 (e.g., the shoulder portion 130 and the body portion 120). To protect the imaging units 310/370, the wall section 392 may include piece of clear plastic or glass 396 (e.g., Gorilla® glass from Corning®) that covers the one or more openings 394A/B.

Like the imaging unit 310 and light source 320 discussed above, the controller may control the operation of the second imaging unit 370 and light source 380, based upon the rotational position output of from the synchronizer 330. For example, the controller may control the exposure of the imaging unit 370 and the pulse of the light source 380 such that the light source pulses/strobes and the imaging unit 380 takes an image at a predetermined rotational position of the separation device 11 (e.g., to generate a stream of images taken at the same rotational position of the bowl 12).

In some embodiments, the controller (e.g., the controller for the imaging system 300 or the controller for the blood processing system) may include a multiplexer that multiplexes the images from each of the imaging units 310/370. For example, the multiplexer can multiplex the images taken from the first and second imaging units 310/370 separately or together (e.g., the multiplexer can create an image/image stream for each imaging unit 310/370 or a single image/image stream from both of the imaging units 310/370). The images/image streams (or a summary of the images/image streams) generated from the first and second imaging units 310/370 may then be sent to a service/maintenance system/ person, who may then monitor the image data to determine (e.g., in real time) if the blood processing system requires service, for example, based on the quality of separation, the locations of the interfaces (e.g., air/plasma interface, plasma/ red blood cell interface, etc.), and/or the movement of the bowl 12. Additionally or alternatively, the images/image streams may be displayed so that the user can monitor the blood processing procedure.

The number of cameras and/or imaging units may vary depending on the application and the bowl 12 used during blood processing. For example, systems and procedures utilizing the Latham type centrifuge bowl shown in FIG. 3 may utilize both imaging units 310/370. However, systems and procedures utilizing other types of bowls (e.g., the blow-molded bowls mentioned above) may only utilize the first imaging unit 310.

It is worth noting that the algorithm used to (1) analyze the images captured by the imaging unit 310, the image data, the interface locations, the dimensions of the buffy coat, etc. and (2) control the imaging system 300 and blood processing system 10 may be dependent upon a number of factors. For example, the algorithm may be dependent upon the color of the light generated by the light source 320, the fluid within the separation device (e.g., whole blood, red cells, plasma, etc.), and/or the characteristics of the blood being processed and its individual components (e.g., hematocrit, platelet count, etc.). Additionally, to compensate for such dependencies, and based upon one or more of the criteria listed above, some embodiments of the present invention may modify/ change the algorithm used to analyze the images/data (e.g., the system 300 may adapt the algorithm to compensate for the change in light color generated by the light source 320, the type of fluid in the bowl 12, etc.).

It is also important to note that various embodiments of the present invention can not only be used during blood processing, but may also be used during initial set up to confirm that proper equipment is being installed and that the separation device 11/bowl 12 is installed properly (e.g., that the bowl 12 is aligned within the system 10). For example, when the separation device 11/bowl 12 is initially installed in the blood processing system 10, the system 10 may rotate the separation device slowly 11 to allow the imaging system 300 to image and record information molded and/or printed on the separation device 11 (e.g., manufacturer information, model/part information, manufacture date, outdate information, expiration date information, inspection information, etc.). The imaging system 300 may then confirm that the installed separation device 11/bowl 12 is suitable for the procedure to be performed (e.g., by comparing the information to a database and/or information previously input into the apheresis system 10). If the imaging system 300 (or the controller) determines that the bowl 12 is not suitable for the procedure, the system 300/controller may prevent the procedure from continuing and alert the operator/technician, for example, by putting a notification on the display and/or activing an alarm.

Additionally or alternatively, in some embodiments, the imaging system 300 can be used to ensure that the separation device 11/bowl 12 is installed properly and is vertically and radially aligned. In such embodiments, the imaging system 300 may image the bowl 12 at more than one location on/rotational position of the bowl 12 (e.g., at 0 and 180 degrees) and analyze the image/image data to determine if the bowl 12 is aligned. For example, if the bowl 12 is both vertically and radially aligned, the position of the bowl 12 (e.g., up and down, and left to right) in the images taken at 0 and 180 degrees should remain the same (e.g. the images should not show the bowl 12 moving). However, if the imaging system 300 detects and the images show that the position of the bowl 12 moving (e.g., up or down, or left to right), the bowl 12 is not aligned properly and should be reinstalled and/or replaced. In such cases, the system 300/controller may stop the bowl 12 and alert the operator/technician.

In order to provide additional feedback regarding system operation, some embodiments may provide for audio and vibration monitoring. In particular, in addition to the imaging unit 320, the imaging system 300 may also include (and the controller may be connected to) a microphone (e.g., a MEM based microphone) that picks up and records any unusual and/or problematic noises generated by the spinning bowl 12, and a vibration sensor (e.g., a multi axis vibration sensor) that measures the amount of vibration of the bowl 12. Both the microphone and the vibration sensor may send an output (e.g., an audio output and a vibration output) to the controller. As with the images captured by the imaging unit 310, the controller may analyze, for example, using a fast Fourier transform (FFT), the sound and vibration output from the microphone and vibration sensor to determine any abnormalities during the blood processing procedure. If any abnormalities are detected, the system 300 (or the controller) may stop the apheresis procedure and alert the operator/technician.

It should be noted that by utilizing the imaging system 300 described above, various embodiments of the present invention are able to provide real-time video inspection of the separation device 11. Additionally, the imaging system 300, in conjunction with the microphone and vibration sensor, help to determine when preventative maintenance may be required. For example, the combined information package provided by the imaging unit 310, microphone, and vibration sensor helps the imaging system 300, the apheresis system 10, and/or the operator/technician identify system abnormalities and changes over time. Additionally, the information about the centrifuge vibration, alignment and bearing noise can be offloaded electronically and analyzed over periods of time to provide trends in performance and predict when maintenance may be required before problems arise.

Although the imaging system 300 described above is discussed in relation to a blood component separation device, other embodiments of the imaging system can be used in different applications. To that end, FIGS. 8A and 8B show an imaging system 500 that can be used to image any number of rotating objects. For example, the imaging system 500 may include an enclosure 510 into which the object 530 to be imaged may be placed (discussed in greater detail below) and a lid 520 that may be placed over the enclosure 510 and the object 530 to be imaged. To allow a user to monitor the interior of the enclosure 510 and the object 530 (e.g., as the object 530 rotates), the lid 520 may include a window 522. Also, to facilitate the opening and closing of the lid 520, the lid 520 may be secured to the enclosure 510 via a hinge 524.

Figure 9:
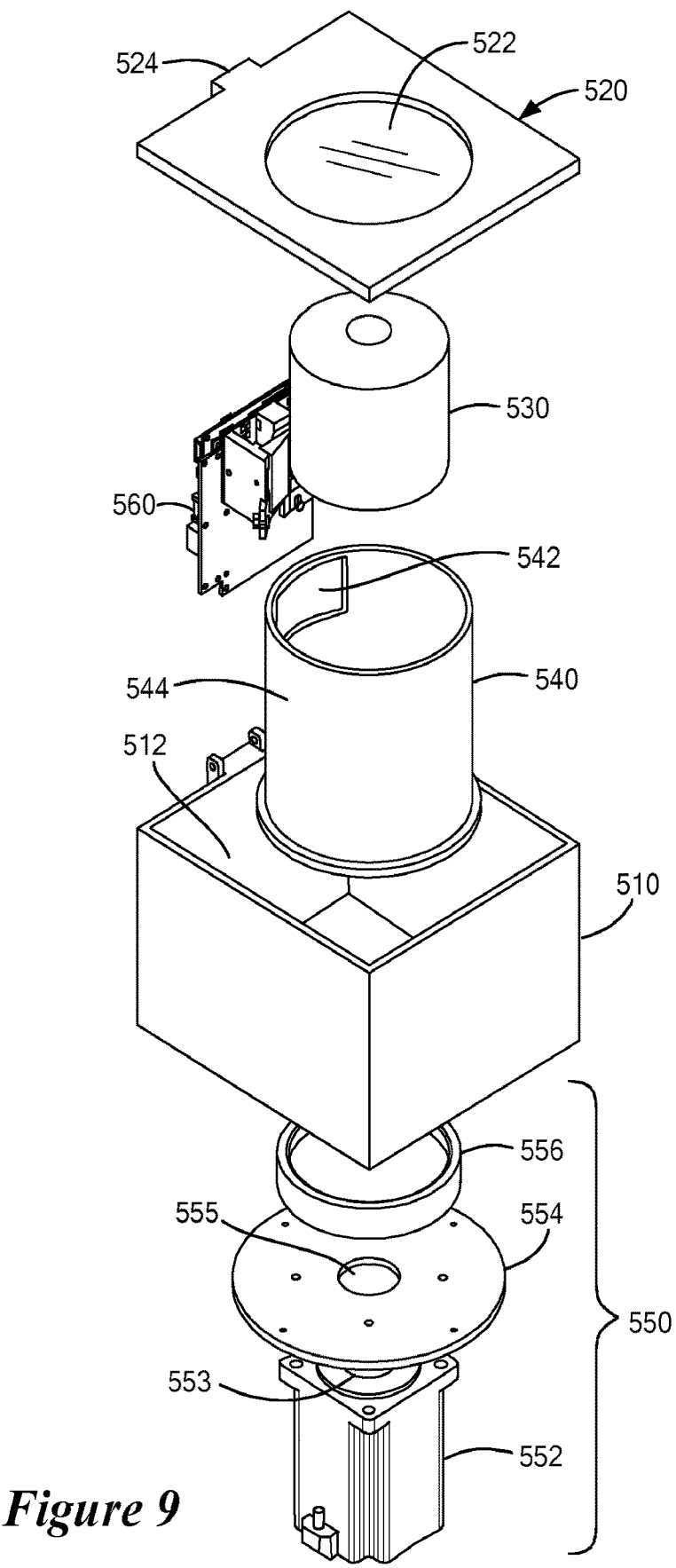
FIG. 9 schematically shows an exploded view of the imaging system shown in FIGS. 8A and 8B, in accordance with some embodiments of the present invention.

As best shown in FIG. 9, within the interior of the enclosure 510, the imaging system 500 can include a chamber 540 in which the object 530 may be placed during imaging. The chamber 540, in turn, can sit on a motor assembly 550 that rotates the object 530 during imaging. For example, the chamber 540 may rest on a turntable 556 that is secured to the drive shaft 553 of the motor 552. The system 500 may also include bottom plate 554 that is secured/attached to the enclosure 510 and has a hole 555 through which the drive shaft 553 may extend. Therefore, as the motor 552 rotates the drive shaft 553, the rotational force will be translated to the turntable 556, causing the chamber 540 and object 530 to rotate.

In a manner similar to that described above for imaging unit 310, the system shown in FIGS. 8A and 8B may also have an imaging unit 560 for imaging the object 530. Like the imaging unit 310, the imaging unit 560 in imaging system 500 may be mounted off the axis of rotation. To that end, the imaging unit 560 may be mounted outside of the chamber 540 (e.g., between an outer wall 544 of the chamber 540 and the inner wall 512 of the enclosure 510). In such embodiments, the chamber 540 may include an opening 542 through which the imaging unit 560 may illuminate and image the object 530.

Figure 10:
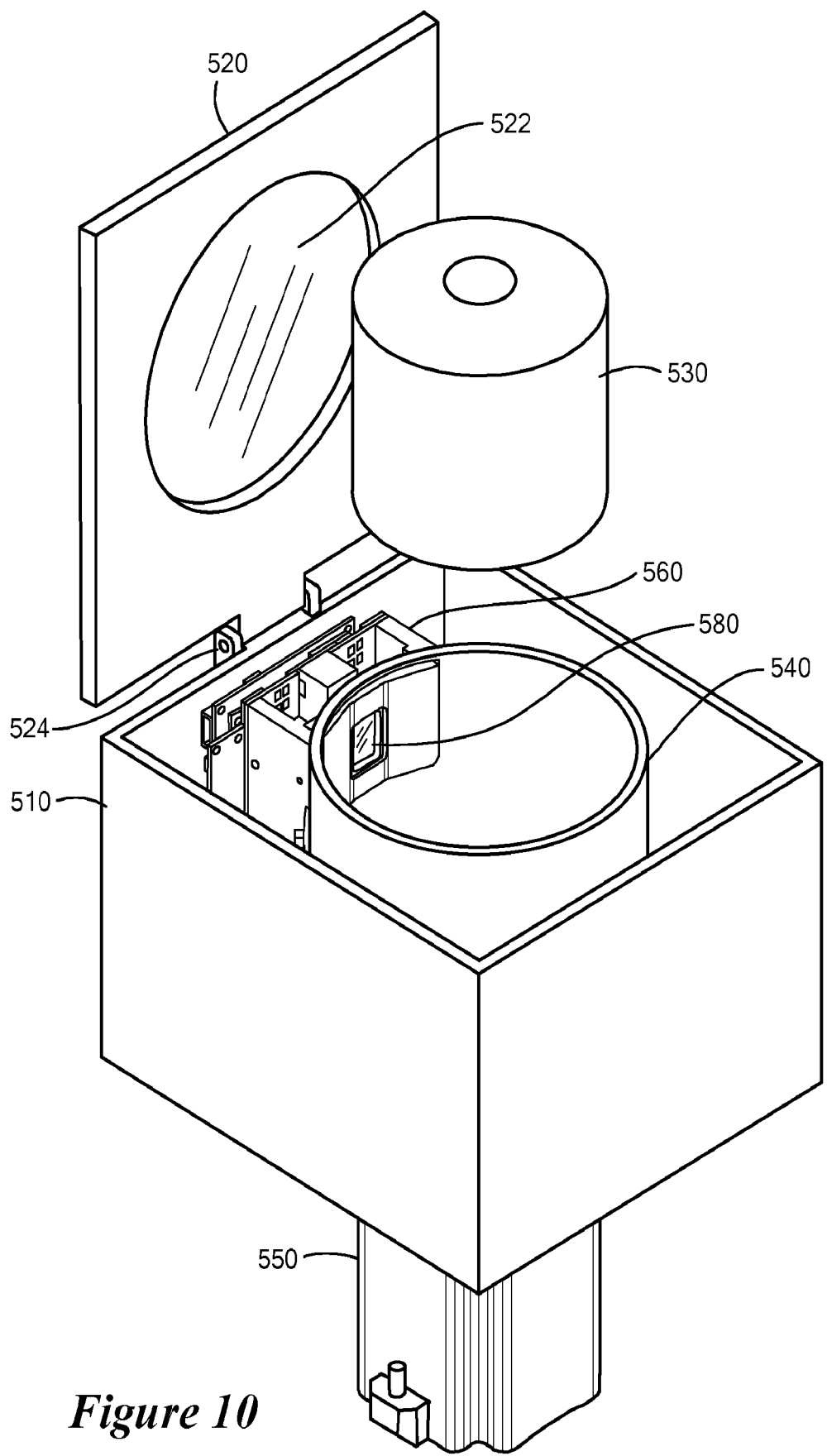
FIG. 10 schematically shows an object being placed in the imaging system shown in FIGS. 8A and 8B, in accordance with some embodiments of the present invention.
Figure 11:
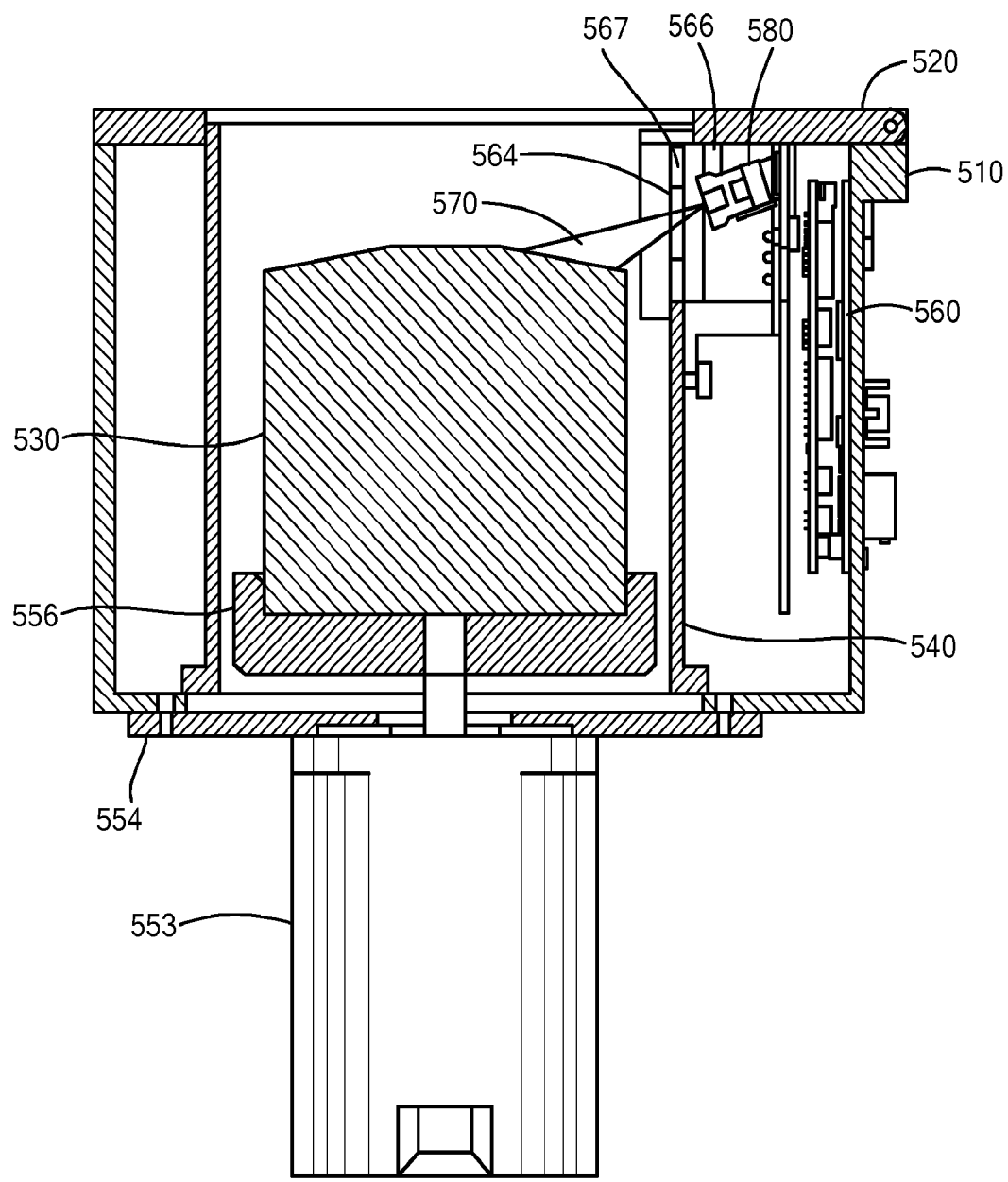
FIG. 11 schematically shows a cross-sectional view of the imaging system shown in FIGS. 8A and 8B with an object to be imaged, in accordance with further embodiments of the present invention.
Figure 12:
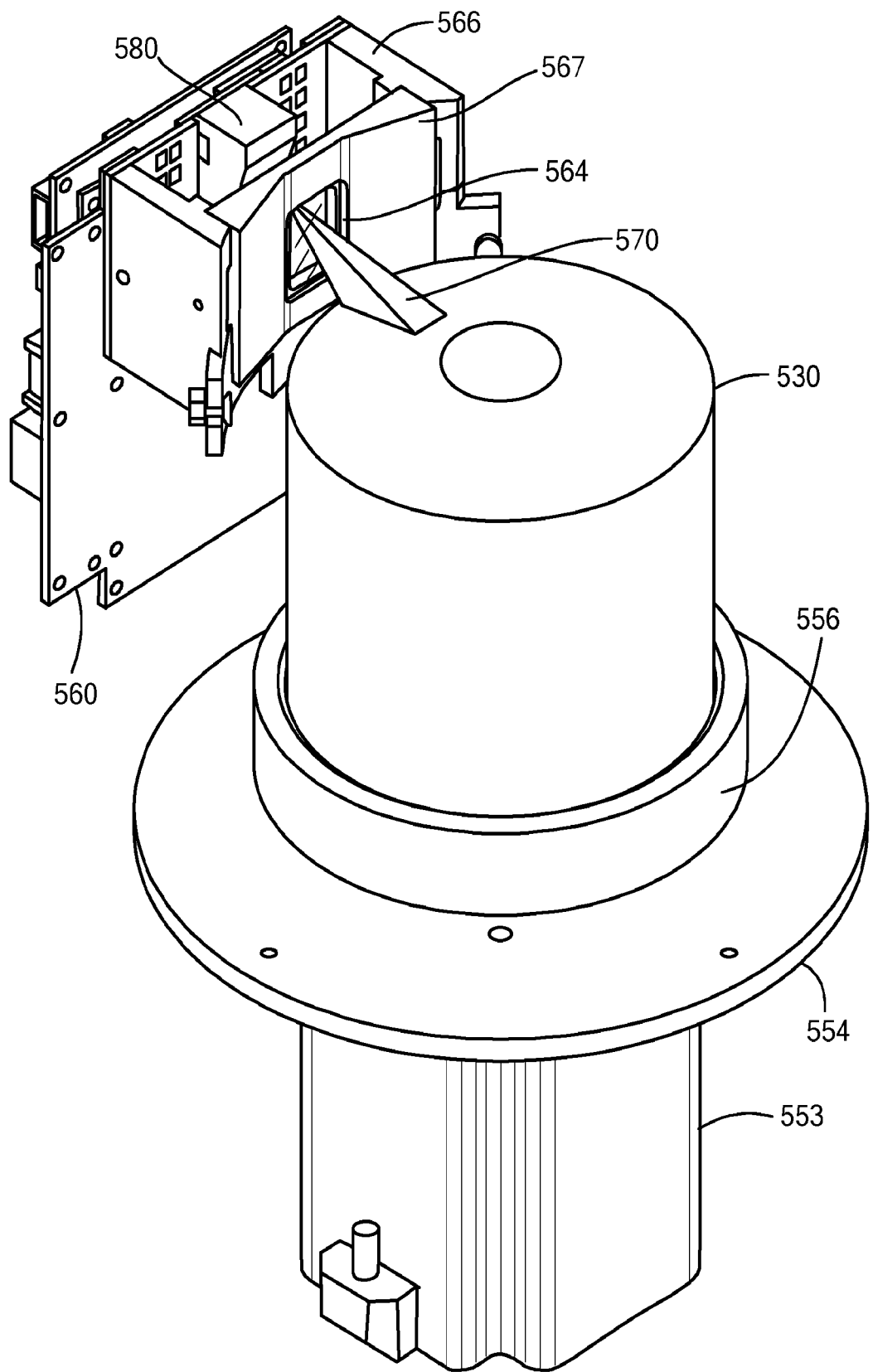
FIG. 12 schematically shows the imaging system shown in FIGS. 8A and 8B with an object to be imaged and the enclosure removed, in accordance with further embodiments of the present invention.

As shown in FIG. 10, when a user wishes to image an object 530, the user may open the lid 520, place the object 530 into the chamber 540 and close the lid 520. Once the object 530 is located within the chamber 540, the imaging unit 560 (e.g., the camera assembly 580) will be located above and off of the rotational axis of the object 530. In this manner and as shown via a trace of the optics/field of view 570 of the imaging unit 560 (FIGS. 11 and 12), the imaging unit 560 will be able to image at least a portion (e.g., the top) of the object 530. Additionally, to protect the imaging unit 560 (e.g., the camera assembly 580), the imaging unit 560 may include a camera enclosure 566 around the camera assembly 580. To allow the camera assembly 580 to view and image the object 530, the camera enclosure 566 may include a window 564 in the front wall 567 of the enclosure 566.

Figure 14:
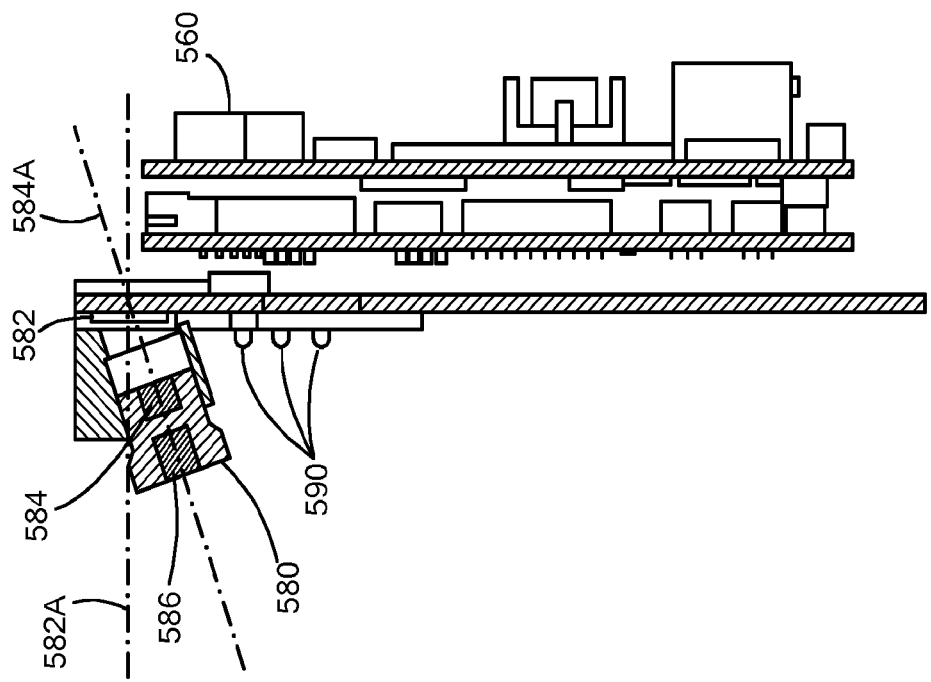
FIG. 14 schematically shows a side view of an imaging unit used within the imaging system shown in FIGS. 8A and 8B, in accordance with some embodiments of the present invention.
Figure 13:
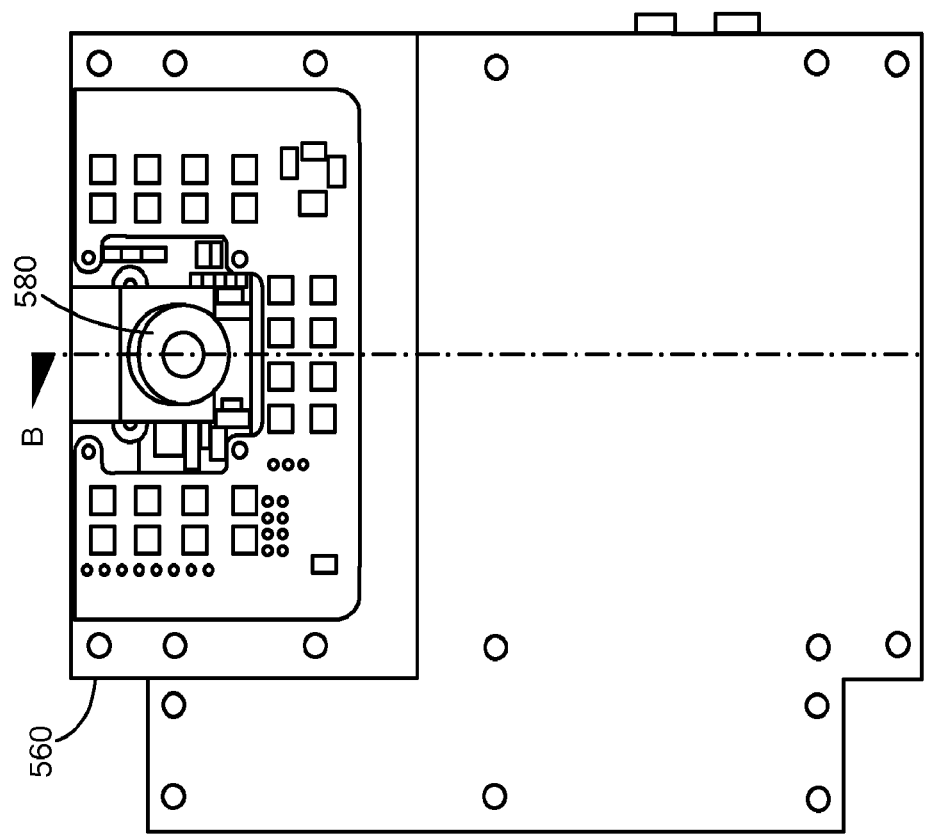
FIG. 13 schematically shows a front view of an imaging unit used within the imaging system shown in FIGS. 8A and 8B, in accordance with some embodiments of the present invention.

FIGS. 13 and 14 schematically show one embodiment of an imaging unit 560 that may be used with the imaging systems discussed above. As shown and as discussed above, the imaging unit 560 may include the camera assembly 580 and a light source 590 that illuminates the object 530. Like the imaging unit 310 discussed above, the camera assembly 580 may include an imaging sensor 582 and one or more lenses 584/586. To ensure that the imaging unit 560 has a clear view of the object 530, the lenses 584/586 may be oriented at angle with respect to the imaging sensor 582. For example, as shown by the dashed lines in FIG. 14, the axis 582A of the imaging sensor 582 is horizontal, whereas the axis/axes 584A of the lenses 584/586 is/are angled downward.

Also like the imaging unit 310 discussed above, in order to image a large portion of the object 530, the imaging unit 560 (e.g., the camera assembly 580, imaging sensor 582, and lenses 584/586) may be oriented/configured according to the Scheimpflug principle. Additionally or alternatively, the camera assembly 580 may utilize a scanning variable focus lens that scans across one or more surfaces of the object 530. In such embodiments, the imaging system 500 (e.g., a controller/microcontroller within the imaging system 500) may stitch together the images taken as the scanning variable focus lens scans the object 530 to obtain a single, clear image of the object 530 (e.g., of the top surface of the object 530).

The light source 590, like the light source 320 discussed above, may include one or more light emitting diodes (LEDs) that pulse to illuminate the object 530 as it rotates. For example, the light source 590 may include an array of LEDS having varying colors (e.g., red, green, blue, etc.) to allow the imaging system 500 to illuminate the object in a number of colors. Additionally or alternatively, the light source 590 may include a white/wide band light source. In such embodiments, the light source 590 may also include a monochromator that selectively separates a predetermined wavelength of light from the wide band light source to illuminate the object 530.

It is important to note that, in order to get uniform illumination of the rotating object 530 (e.g., uniform illumination of the area being imaged) some embodiments of the present invention may utilize a diffuser to appropriately diffuse the light generated from the light source 590. For example, the system 500 (or the imaging unit 560) may include a scattering diffuser and/or microlens diffuser to diffuse the light generated by the light source 590 and obtain the desired light pattern/uniformity on the object 530.

Figure 15:
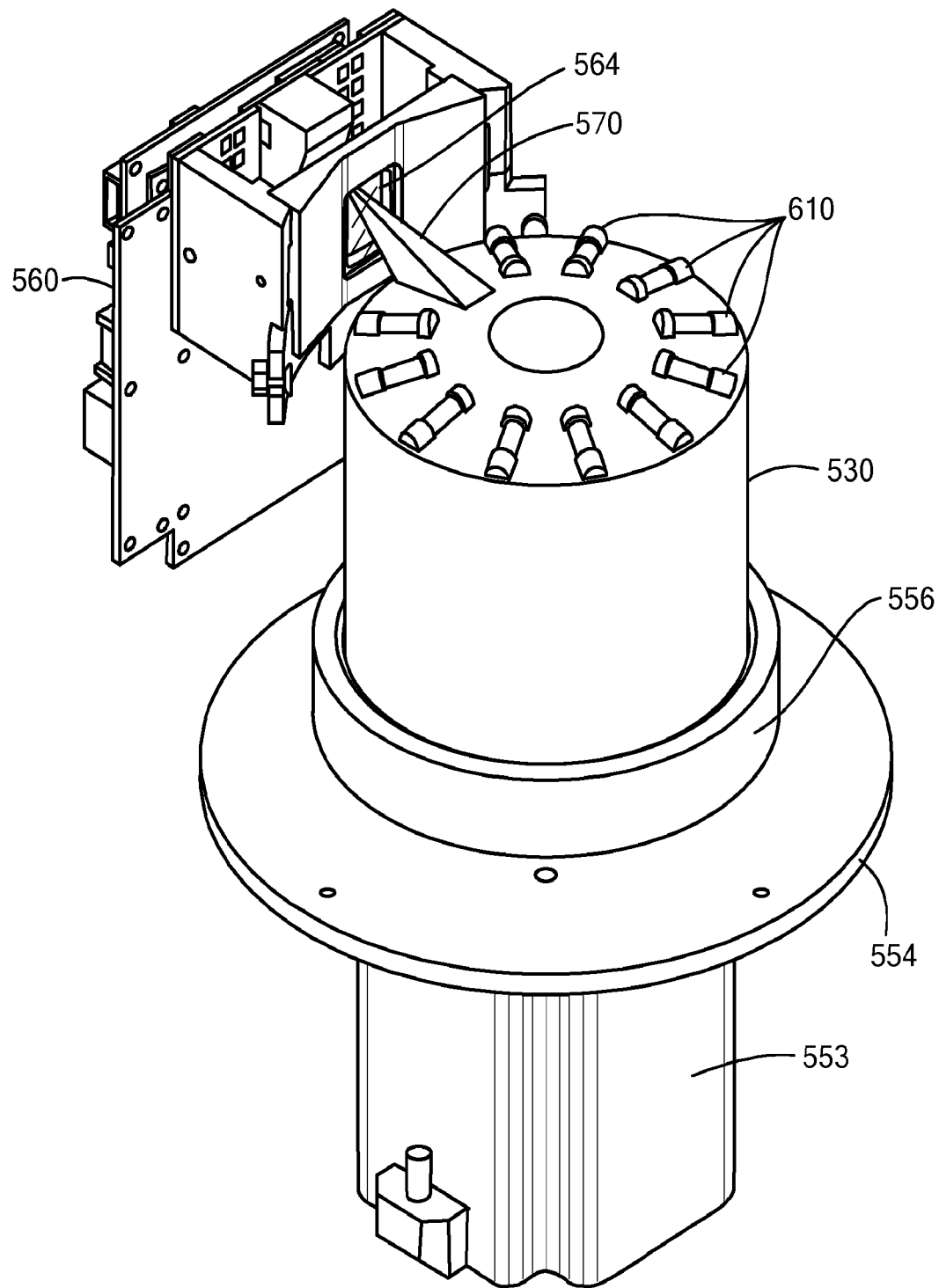
FIG. 15 schematically shows a perspective view of a further alternative imaging system, in accordance with further embodiments of the present invention.

Although the embodiments discussed above image the top of the rotating object 530, other embodiments of the present invention may image individual components located on/within the rotating object. To that end, as shown in FIG. 15, a number of components 610 may be placed on the top surface of the rotating object 530 and the imaging unit 560 may take images of each of the individual components 610 as the rotating object 530 rotates. The images obtained by the imaging unit 560 may then be used to determine one or more characteristics of the components 610. For example, if the components 610 are manufactured parts or similar components, the images may be used to determine the dimensions of each of the parts/components (e.g., to ensure that they are within manufacturing tolerances) and/or confirm the uniformity of the parts/components 610 (e.g., by comparing the images of each of the parts/components 610 to one another).

Alternatively, some embodiments of the present invention may be used to measure a level of blood cell agglutination. In such embodiments, each of the components may be tubes containing a blood sample and a reagent, and the rotating object 530 may act as a centrifuge. For example, the tubes may be loaded on the rotating object 530 (e.g., as shown in FIG. 15), and the rotating object 530 rotated to create a reaction in the tube. The imaging unit 560 may then take images of each of the tubes as the object 530 rotates. The controller and/or microprocessor may then analyze the images and image data to determine the level of agglutination within each of the tubes.

Additionally alternatively, the rotating object 530 may include a number of chambers (not shown) in which a variety of blood bags or samples may be placed (e.g., one bag/sample per chamber or multiple bags/samples per chamber). In such embodiments, the rotation of the object 530 may act to centrifuge the blood/sample, causing the blood to separate into its individual components (e.g., red blood cells, platelets, plasma etc.). As the object 530 rotates and the blood begins to separate, the imaging unit 560 may take images of each of the chambers to determine the level of blood separation in each of the chambers and/or blood bags.

Figure 17:
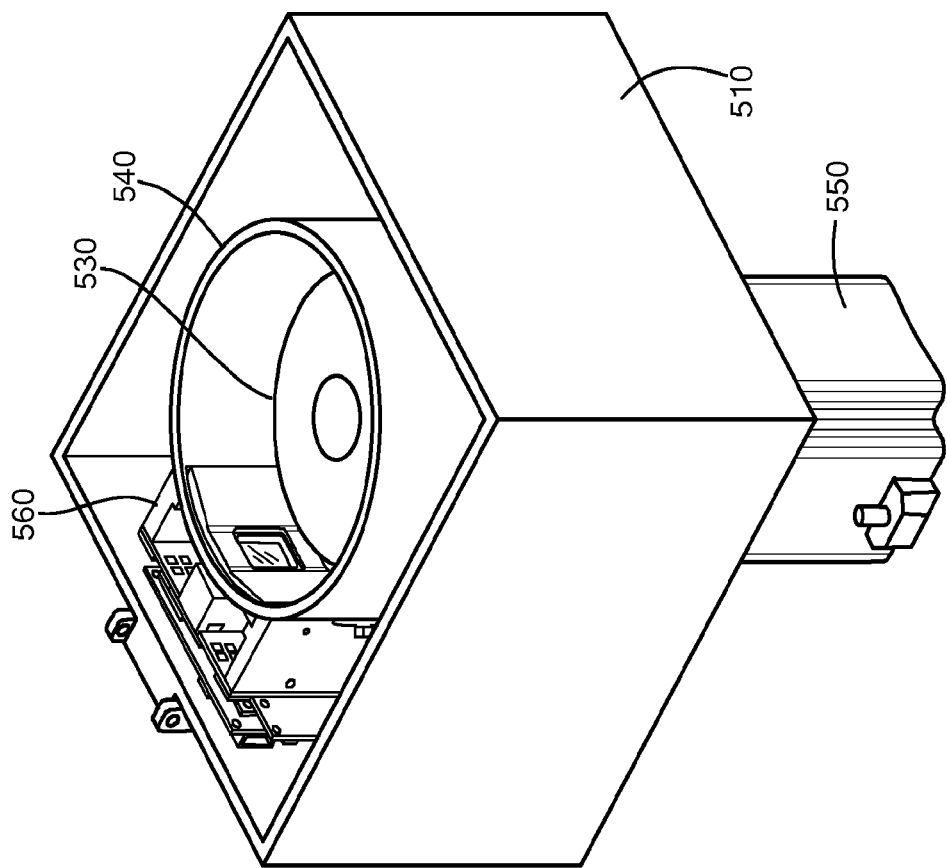
FIG. 17 schematically shows a perspective view of yet another alternative imaging system, in accordance with further embodiments of the present invention.
Figure 16:
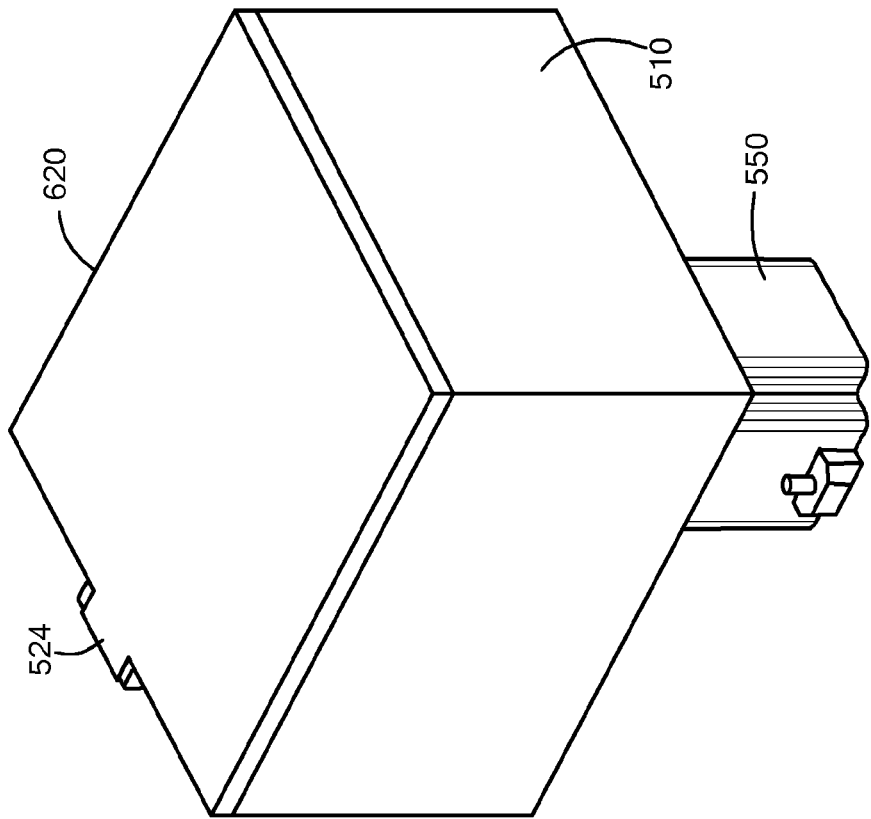
FIG. 16 schematically shows a perspective view of an additional alternative imaging system, in accordance with further embodiments of the present invention.
Figure 18B:
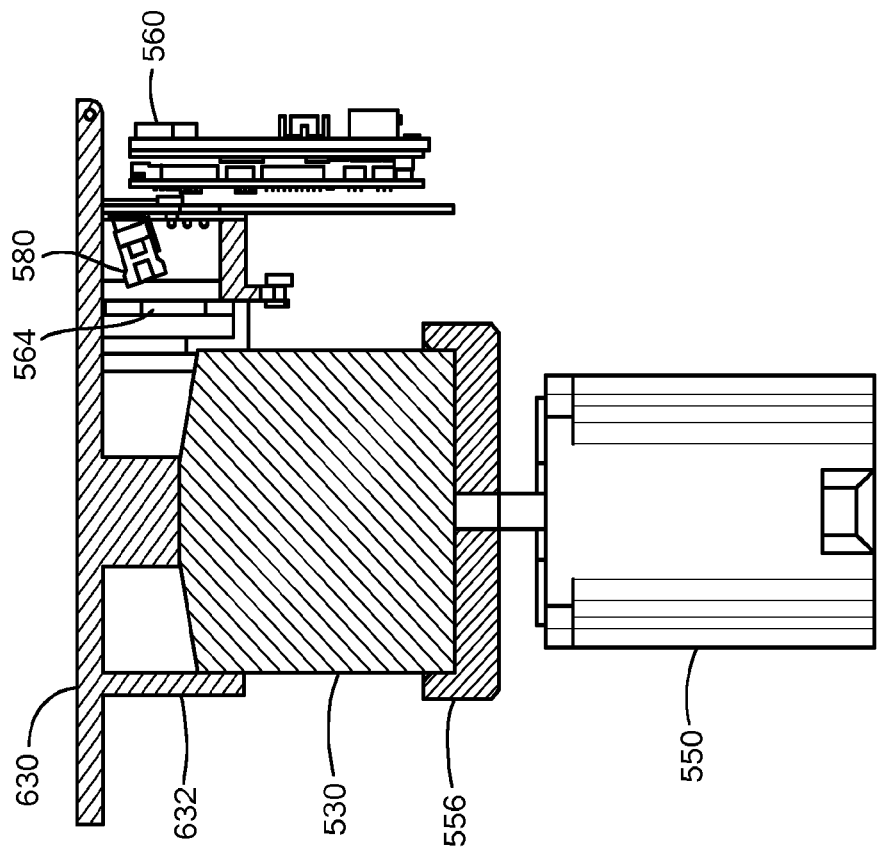
FIGS. 18A and 18B schematically show a side and cross-sectional views of a further alternative imaging system, in accordance with further embodiments of the present invention.
Figure 18A:
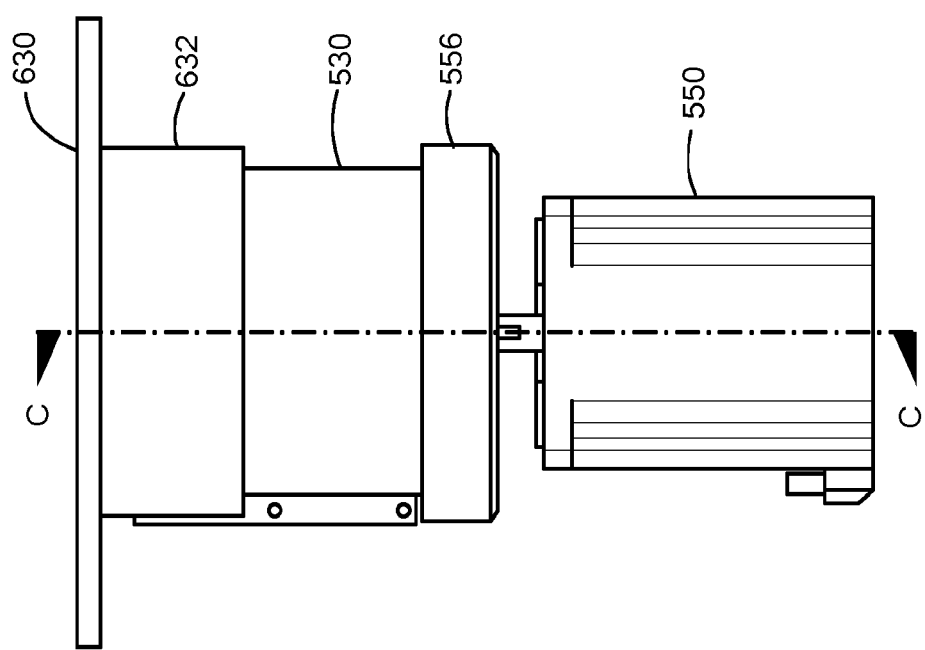

Although some of the embodiments discussed above utilize a lid 520 with a window 522, other embodiments may utilize different lid structures. For example, as shown in FIG. 16, some embodiments may include a solid lid 620 (e.g., a lid without a window 522) to prevent users from seeing into the interior of the enclosure 510. Conversely, other embodiments may not include a lid at all (e.g., the enclosure 510 may be open) (FIG. 17). Additionally or alternatively, the system 500 may utilize a lid 630 with a support structure 632 that extends downward from the lid 630 toward the rotating object 530. As best shown in FIGS. 18A and 18B, the support structure 632 may support the rotating object 530 to prevent the object 530 from shifting side to side or up and down while the object 530 spins/rotates.

It is important to note that, although the embodiments described above directly image the separation device 11/bowl 12 and/or rotating object 530 (e.g., the imaging units 370/560 are aimed at the separation device 11/bowl 12 and/or rotating object 530), other embodiments may image a reflection of the separation device 11/bowl 12 and/or rotating object 530. To that end, the system (e.g., imaging system 300 or system 500) may include a mirror (not shown) that reflects an image of the object (e.g., the separation device 11/bowl 12 and/or rotating object 530) toward the imaging units 310/370/560 and allows the systems to indirectly image the object. In such embodiments, the systems 300/500 may use the optics arrangements discussed above (e.g., Scheimpflug) or the system may use more conventional optics configurations.

The mirror used to reflect the image plane toward the imaging units 310/370/560 may be a standard stationary mirror or a mirror with beam steering capabilities. For example, the mirror may be a MEMS mirror that may be manipulated (e.g., by the controller) to direct the reflection of the separation device 11/bowl 12 and/or rotating object 530 towards the imaging units 310/370/560. Additionally, the beam steering capabilities of a MEMS mirror allows the mirror to scan across the surface of the object 530 and increase the field of view. The images taken as the mirror scans may then be stitched together by the controller to obtain a single image of the object.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. An imaging system for a rotatable object comprising:
   an imaging device configured to take a series of images of at least a portion of the rotatable object, the rotatable object configured to rotate about an axis, the imaging device including a lens defining a lens plane and an image sensor defining an image plane, the lens plane not parallel to the image plane;
   a light source directed at the rotatable object and configured to generate pulses of light that illuminate the at least a portion of the rotatable object during rotation of the rotatable object, thereby allowing the imaging device to take the series of images of the at least a portion of the rotatable object;
   a synchronizer configured to monitor a rotational position of the rotatable object as it rotates; and
   a controller in communication with the imaging device, the light source, and the synchronizer and configured to control the operation of at least one of the imaging device and/or the light source based upon the rotational position of the rotatable object such that each of the series of images is taken at the same rotational position of the rotatable object.

2. An imaging system according to claim 1, wherein the light source is a monochromatic light source.

3. An imaging system according to claim 1, wherein the light source is a wide band light source.

4. An imaging system according to claim 3, wherein the imaging system includes a monochromator configured to selectively separate a predetermined wavelength of light from the wide band light source.

5. An imaging system according to claim 1, wherein the imaging device is off-set from the axis of rotation of the rotatable object.

6. An imaging system according to claim 1, wherein the lens and/or the image sensor is oriented at an angle with respect to the at least a portion of the rotatable object.

7. An imaging system according to claim 6, wherein the lens, image sensor, and the at least a portion of the rotatable object are oriented and positioned according to the Scheimpflug principle.

8. An imaging system according to claim 6, wherein the lens is a scanning variable focus lens configured to scan across a top surface of the rotatable object, the image sensor capturing a plurality of images of the top surface of the rotatable object as the scanning variable focus lens scans.

9. An imaging system according to claim 8, wherein the controller is further configured to stitch together the plurality of images of the top surface, thereby obtaining an image of the top surface of the rotatable object.

10. An imaging system according to claim 6, wherein the lens is a wide angle lens.

11. An imaging system according to claim 6, further comprising a mirror located above a top surface of the rotatable object and configured to generate a reflection of at least a portion of the rotatable object, the imaging device focused on the mirror such that the series of images of at least a portion rotatable object includes a series of images of the reflection.

12. An imaging system according to claim 11, wherein the mirror is a MEMS mirror, the controller in communication with the MEMS mirror and configured to adjust the MEMS mirror to cause the MEMS mirror to scan across the at least a portion of the rotatable object.

13. An imaging system according to claim 1, wherein the rotatable object is a blood processing device.

14. An imaging system according to claim 13, wherein the blood processing device includes one or more chambers configured to hold one or more blood storage containers, the imaging device configured to take a series of images of the one or more blood storage containers.

15. An imaging system according to claim 14, wherein the controller is further configured to determine a level of separation of blood contained within the one or more blood storage containers.

16. An imaging system according to claim 1, wherein the rotatable object is configured to hold one or more fluid samples, the imaging device configured to take a series of images of the one or more fluid samples.

17. An imaging system according to claim 16, wherein the fluid samples are reagents, the controller configured to determine a level of agglutination.

18. An imaging system according to claim 1, wherein the rotatable object includes a plurality of parts located on a surface of the rotatable object, the imaging device configured to take images of each of the plurality of parts.

19. An imaging system according to claim 18, wherein the controller is configured to determine one or more measurements of each of the plurality of parts based on the images of the each of the plurality of parts.

20. An imaging system according to claim 19, wherein the controller is further configured to determine a level of uniformity between the plurality of parts based on the one or more measurements.

21. An imaging system according to claim 1, wherein the light source includes a microlens diffuser configured to diffuse the light generate by the light source.

22. An imaging system according to claim 1, further comprising:
an enclosure having a chamber within an interior of the enclosure and a lid configured to selectively close the enclosure, the rotatable object located within the chamber during rotation.

23. An imaging system according to claim 22, wherein the lid includes a window.

24. An imaging system according to claim 22, wherein the lid includes a support structure extending downward from the lid toward the rotatable object, the support structure configured to support the rotatable object as the object rotates.

25. An imaging system according to claim 22 further comprising:
a turntable configured to support the chamber;
a motor configured to rotate the turntable and the rotatable object; and
a drive shaft operably coupling the motor and the turntable.

26. An imaging system according to claim 25, further comprising a bottom plate located below and secured to the chamber, the bottom plate having an opening, the drive shaft configured to extend through the opening.

27. A method of imaging a rotating object comprising:
rotating an object about and axis;
monitoring the rotational position of the object as it rotates;
pulsing a light source to illuminate at least a portion of the rotating object;
taking, using an imaging device, a first image of the at least a portion of the rotating object as the rotating object rotates, the first image being taken at a first rotational position of the rotating object and when the at least a portion of the rotating object is illuminated by the light source, wherein the imaging device includes a lens defining a lens plane and an image sensor defining an image plane, the lens plane not parallel to the image plane;
taking, using the imaging device, a second image of the at least a portion of rotating object as the rotating object, the second image being taken at a second rotational position and when the at least a portion of the rotating object is illuminated by the light source; and
analyzing the first and second images to determine at least one characteristic of the rotating object.

28. An imaging system for a blood processing device comprising:
an imaging device configured to take a series of images of at least a portion of a blood component separation device, the blood component separation device configured to rotate about an axis and separate whole blood into a plurality of blood components, wherein the imaging device includes a lens defining a lens plane and an image sensor defining an image plane, the lens plane not parallel to the image plane;
a light source directed at the blood component separation device and configured to generate pulses of light that illuminate the at least a portion of the blood component separation device during rotation of the blood component separation device, thereby allowing the imaging device to take the series of images of the at least a portion of the blood component separation device;
a synchronizer configured to monitor a rotational position of the blood component separation device; and
a controller in communication with the imaging device, the light source, and the synchronizer and configured to control the operation of at least one of the imaging device and/or the light source based upon the rotational position of the blood component separation device such that each of the series of images is taken at the same rotational position of the blood component separation device.

29. An imaging system according to claim 28, wherein the synchronizer is an angular encoder.

30. An imaging system according to claim 28, wherein the synchronizer is located on a shaft of the blood component separation device.

31. An imaging system according to claim 28, further comprising a visual display configured to display the series of images.

32. An imaging system according to claim 31, wherein the series of images are jitter free.

33. An imaging system according to claim 31, wherein the series of images includes a visual representation of an interface between at least two of the plurality of blood components.

34. An imaging system according to claim 33, wherein the controller is further configured to control an operation of the blood processing device based, at least in part, on a location of the interface between at least two of the plurality of blood components.

35. An imaging system according to claim 28, wherein the imaging device is a solid state imager.

36. An imaging system according to claim 28, wherein the imaging device includes a CMOS sensor.

37. An imaging system according to claim 28, wherein the lens and/or the image sensor is oriented at an angle with respect to the at least a portion of the blood component separation device.

38. An imaging system according to claim 37, wherein the lens, image sensor, and the at least a portion of the blood component separation device are oriented and positioned according to the Scheimpflug principle.

39. An imaging system according to claim 28, wherein the light source includes a plurality of light emitting diodes having varying colors.

40. An imaging system according to claim 39, wherein a color of the generated pulse of light is based, at least in part, upon a characteristic of the whole blood to be processed or a characteristic of at least one of the plurality of blood components.

41. An imaging system according to claim 28, further comprising:
a microphone configured to pick up a sound of the blood component separation device during rotation and generate and audio output representative of the sound.

42. An imaging system according to claim 41, wherein the controller is in electrical communication with the microphone and is configured to receive the audio output and control the operation of the blood processing device based upon the audio output.

43. An imaging system according to claim 42, wherein the controller is in electrical communication with the microphone and is configured to receive the audio output, analyze the audio output over a period of time, and determine a performance trend.

44. An imaging system according to claim 41, wherein the microphone is a MEMS microphone.

45. An imaging system according to claim 28, further comprising:
a vibration sensor configured to measure the vibration of the blood component separation device during rotation and generate a vibration output representative of the vibration.

46. An image system according to claim 45, wherein the controller is in electrical communication with the vibration sensor and is configured to receive the vibration output and control the operation of the blood processing device based upon the vibration output.

47. An imaging system according to claim 46, wherein the controller is in electrical communication with the vibration sensor and is configured to receive the vibration output, analyze the vibration output over a period of time, and determine a performance trend.

48. An imaging system according to claim 45, wherein the vibration sensor is a multi-axis accelerometer.

49. An imaging system according to claim 28, wherein the imaging device is configured to read information contained on the blood component separation device.

50. An imaging system according to claim 49, wherein the information contains at least one selected from the group consisting of manufacturer information, a model number, a part number, a manufacture date, outdate information, expiration date information, and inspection information.

51. An imaging system according to claim 28, further comprising:
a second imaging device configured to take a series of images of a second portion of the blood component separation device; and
a second light source directed at the blood component separation device and configured to generate pulses of light that illuminate the second portion of the blood component separation device during rotation of the blood component separation device, thereby allowing the second imaging device to take the series of images of the second portion of the blood component separation device, wherein the controller is further configured to control the operation of the second imaging device and/or the second light source based upon the rotational position of the blood component separation device such that each of the series of images of the second portion is taken at the same rotational position of the blood component separation device.

52. An imaging system according to claim 51, wherein the second imaging device includes a wide angle lens and an image sensor.

53. An imaging system according to claim 51, wherein the second portion of the blood component separation device is a body portion.

54. An imaging system according to claim 28, wherein the imaging device is configured to take a first image at a first location on the blood component separation device and a second image at a second location on the blood component separation device.

55. An imaging system according to claim 54, wherein the controller is further configured to analyze the first image and the second image and determine if the blood component separation device is aligned.

* * * * *